(12) United States Patent
Hu et al.

(10) Patent No.: US 9,458,106 B2
(45) Date of Patent: Oct. 4, 2016

(54) PHENYL-PYRIDINE/PYRAZINE AMIDES FOR THE TREATMENT OF CANCER

(71) Applicant: Hoffmann-La Roche Inc., Little Falls, NJ (US)

(72) Inventors: Hui Hu, Shanghai (CN); Min Jiang, Shanghai (CN); Taiguang Jin, Shanghai (CN); Rui Niu, Shanghai (CN); Jianhua Wang, Shanghai (CN); Min Wang, Shanghai (CN); Song Yang, Shanghai (CN); Taichang Yuan, Shanghai (CN); Chengang Zhou, Shanghai (CN); Zheng Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/628,103

(22) Filed: Feb. 20, 2015

(65) Prior Publication Data
US 2015/0158815 A1   Jun. 11, 2015

Related U.S. Application Data

(63) Continuation of application No. PCT/EP2013/067224, filed on Aug. 19, 2013.

(51) Int. Cl.
| C07D 213/74 | (2006.01) |
| A61K 31/4418 | (2006.01) |
| C07D 213/81 | (2006.01) |
| C07D 409/12 | (2006.01) |
| C07D 241/20 | (2006.01) |
| C07D 401/04 | (2006.01) |
| C07D 401/12 | (2006.01) |

(52) U.S. Cl.
CPC ......... *C07D 213/74* (2013.01); *A61K 31/4418* (2013.01); *C07D 213/81* (2013.01); *C07D 241/20* (2013.01); *C07D 401/04* (2013.01); *C07D 401/12* (2013.01); *C07D 409/12* (2013.01)

(58) Field of Classification Search
CPC .................. C07D 213/74; A61K 31/4418
See application file for complete search history.

(56) References Cited

U.S. PATENT DOCUMENTS

2008/0085906 A1* 4/2008 Andjelkovic et al. ... 514/255.06

FOREIGN PATENT DOCUMENTS

| WO | 2008/040651 | 4/2008 | |
| WO | 2008/079933 | 7/2008 | |
| WO | 2011/116786 | 9/2011 | |
| WO | 2011/137022 | 11/2011 | |
| WO | 2013/004332 | 1/2013 | |
| WO | WO 2013/116786 | * 11/2013 | ........... A61K 31/517 |

OTHER PUBLICATIONS

T. Rzymski, et al., CDK8 kinase-An emerging target in targeted cancer therapy, Biochim. Biophys. Acta (2015), dx.doi.org/10.1016/j.bbapap.2015.05.011.*

* cited by examiner

*Primary Examiner* — Robert Havlin
(74) *Attorney, Agent, or Firm* — Tony Wei Peng

(57) ABSTRACT

The invention provides novel compounds having the general formula:

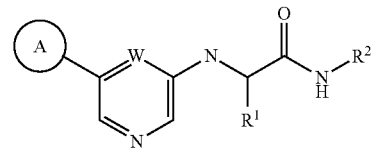

wherein $R^1$, $R^2$, A and W are as described herein, compositions including the compounds and methods of using the compounds.

13 Claims, No Drawings

PHENYL-PYRIDINE/PYRAZINE AMIDES FOR THE TREATMENT OF CANCER

CROSS REFERENCE TO RELATED APPLICATIONS

This application is a continuation of PCT/EP2013/067224 filed on Aug. 19, 2013, which claims priority to PCT/CN2012/080487 filed Aug. 23, 2012, the disclosures of which are incorporated herein by reference in their entirety.

The present invention relates to organic compounds useful for therapy in a mammal, and in particular to inhibit cell proliferation and induce cell cycle arrest and apoptosis that overexpress CDK8 or Cyclin C useful for treating cancer.

FIELD OF THE INVENTION

The cyclin-dependent kinase (CDK) complexes are well-conserved Ser/Thr kinase family, and it has been shown to be activated by the binding of regulatory partner, generally a cyclin. There are total 20 CDK family members and 5 CDK-like proteins based on the similarities in sequence and function. CDKs regulate various key transitions of cell cycle and play an important role in the regulation of transcription, apoptosis and neuronal functions.

Dysregulation of CDKs has been linked to pathological events and both proliferative and non-proliferative disease, including cancers, Alzhemers disease (AD), parkinson's disease, Stroke/ischemia, pain, traumatic brain injury, kidney disease, inflammation pathologies, type 2 diabetes, viral infection (HSV, HCMV, HPV, HIV).

CDK8 is a CyclinC-dependent CDK family kinase and functions as a transcriptional regulator. Several phosphorylation targets of CDK8 have been identified, including the RNA polymerase II (RNAPII) C-terminal domain (CTD), histone H3, subunits of general transcription factors (GTFs) and certain transactivators. CDK8 has also been described as a transcriptional coactivator in oncongenic signaling pathways, including the β-catenin pathway, the serum response network, the Tumor Growth Factor TGFβ signaling pathway, the p53 pathway, as well as in thyroid hormone-dependent transcription. Colocalization of CDK8 and Cyclin C was also reported in neurodegenerative disease such as AD. CDK8 was found to be frequently dysregulated in various human cancers, such as colon cancer, gastric cancer and melanoma. Inhibition of CDK8 by short hairpin RNA (shRNA) inhibits cancer cell proliferation, and induces cell cycle arrest and apoptosis in vitro and in vivo models. Although Silibinin, the major active constituent of silymarin isolated from milk thistle (Silybum marianum), has shown strong cell growth inhibition in colon cancer through down-regulation CDK8 expression, there are no known direct CDK8 inhibitors under clinical development. Therefore, there is a great unmet medical need to develop CDK8 inhibitors for cancer patients.

SUMMARY OF THE INVENTION

Objects of the present invention are novel compounds of formula I, their manufacture, medicaments based on a compound in accordance with the invention and their production as well as the use of compounds of formula I for the treatment of cancer.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl, tert-butyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "halogen" means fluorine, chlorine, bromine or iodine. Halogen is particularly fluorine or chlorine.

The term "hydroxy" alone or in combination refers to the group —OH.

The term "carbonyl" alone or in combination refers to the group —C(O)—.

The term "sulfonyl" alone or in combination refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of CDK8 or Cyclin C

The present invention provides novel compounds having the general formula I:

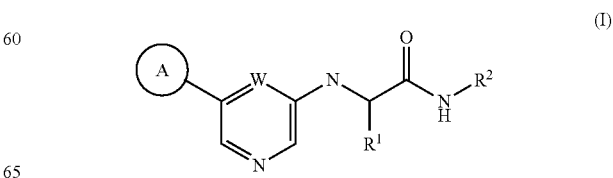

wherein $R^1$ is phenyl, pyridinyl, thienyl, pyrimidinyl, pyrazolyl, pyridinonyl or pyrrolyl; which is unsubstituted or once or twice substituted by $C_{1-6}$alkoxy, $C_{1-6}$alkyl, halogen or trifluoromethyl;

$R^2$ is hydrogen, $C_{1-6}$alkyl, $C_{1-6}$alkylcarbonyl or $C_{1-6}$alkylsulfonyl;

A is phenyl, pyridinyl, pyridinonyl, thienyl, pyrazolyl or pyrrolyl; which is unsubstituted or once or twice or thrice substituted by $C_{1-6}$alkoxy, $C_{1-6}$alkyl, cyano, halogen, hydroxy or trifluoromethyl;

W is —N— or —CH;

or pharmaceutically acceptable salt thereof.

Another embodiment of present invention is (ii) a compound of formula I, wherein $R^1$ is phenyl, which is unsubstituted or once or twice substituted by $C_{1-6}$alkoxy, $C_{1-6}$alkyl or halogen; pyridinyl; or thienyl;

$R^2$ is hydrogen or $C_{1-6}$alkylsulfonyl;

A is phenyl or pyridinyl; which is once or twice or thrice substituted by $C_{1-6}$alkoxy, $C_{1-6}$alkyl, halogen or hydroxy;

W is —N— or —CH;

or pharmaceutically acceptable salt thereof

Further embodiment of present invention is (iii) a compound of formula I, wherein $R^1$ is phenyl, which is unsubstituted or once or twice substituted by methoxy, methyl, fluoro or chloro; pyridinyl; or thienyl;

$R^2$ is hydrogen or methylsulfonyl;

A is phenyl or pyridinyl; which is once or twice or thrice substituted by ethoxy, methoxy, methyl, fluoro, chloro or hydroxy;

W is —N— or —CH;

or pharmaceutically acceptable salt thereof.

Another embodiment of present invention is (iv) a compound of formula I or a pharmaceutically acceptable salt thereof, wherein $R^1$ is phenyl, which is unsubstituted or once or twice substituted by $C_{1-6}$alkoxy, $C_{1-6}$alkyl or halogen; pyridinyl; or thienyl;

$R^2$ is hydrogen;

A is phenyl or pyridinyl; which is once or twice or thrice substituted by $C_{1-6}$alkoxy, $C_{1-6}$alkyl, halogen or hydroxy;

W is —CH.

Further embodiment of present invention is (v) a compound of formula I or a pharmaceutically acceptable salt thereof, wherein $R^1$ is phenyl, which is unsubstituted or once or twice substituted by methoxy, methyl, fluoro or chloro; pyridinyl; or thienyl;

$R^2$ is hydrogen;

A is phenyl or pyridinyl; which is once or twice or thrice substituted by ethoxy, methoxy, methyl, fluoro, chloro or hydroxy;

W is —CH.

Another embodiment of present invention is (vi) a compound of formula I or a pharmaceutically acceptable salt thereof, wherein $R^1$ is phenyl;

$R^2$ is hydrogen;

A is phenyl, which is once or twice substituted by $C_{1-6}$alkoxy, halogen or hydroxy; W is —N—.

Further embodiment of present invention is (vii) a compound of formula I or a pharmaceutically acceptable salt thereof, wherein $R^1$ is phenyl;

$R^2$ is hydrogen;

A is phenyl, which is once or twice substituted by methoxy, fluoro, chloro or hydroxy;

W is —N—.

Particular compounds of formula I, including their activity data, NMR data and MS data are summarized in the following Table 1, 2 and 3.

TABLE 1

Structure, name and activity data of particular compounds

| Example No. | Structure | Name | IC$_{50}$ (μM) |
|---|---|---|---|
| 1 | 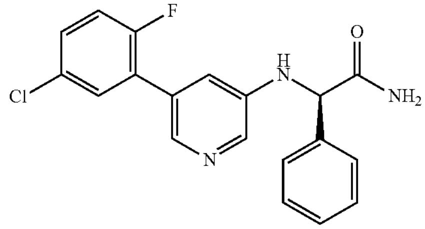 | (R)-2-[5-(5-Chloro-2-fluoro-phenyl)-pyridin-3-ylamino]-2-phenyl-cetamide | 0.0917 |
| 2 | 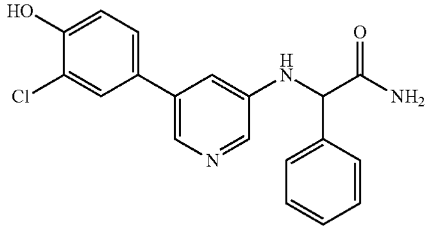 [SMILES: NC(=O)C(Nc1cncc(-c2ccc(O)c(Cl)c2)c1)c1ccccc1] | 2-[5-(3-Chloro-4-hydroxy-phenyl)-pyridin-3-ylamino]-2-phenyl-acetamide | 0.1051 |

TABLE 1-continued

Structure, name and activity data of particular compounds

| Example No. | Structure | Name | IC$_{50}$ (µM) |
|---|---|---|---|
| 3 | 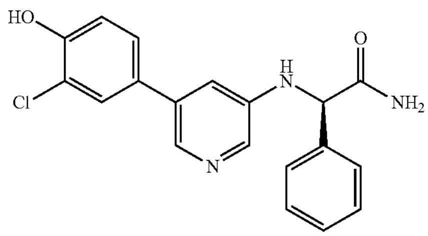 [SMILES: NC(=O)[C@H](Nc1cncc(-c2ccc(O)c(Cl)c2)c1)c1ccccc1] | (R)-2-[5-(3-Chloro-4-hydroxy-phenyl)-pyridin-3-ylamino]-2-phenyl-acetamide | 0.0071 |
| 4 | 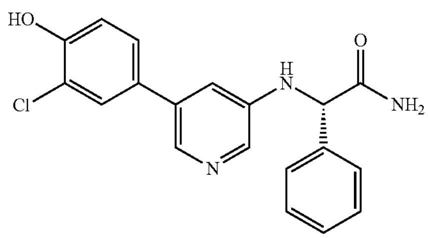 | (S)-2-[5-(3-Chloro-4-hydroxy-phenyl)-pyridin-3-ylamino]-2-phenyl-acetamide | 0.4712 |
| 5 | 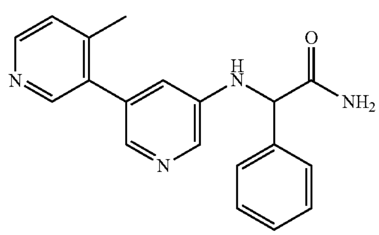 [SMILES: Cc1ccncc1-c1cncc(NC(C(N)=O)c2ccccc2)c1] | 2-(4'-Methyl-[3,3']bipyridinyl-5-ylamino)-2-phenyl-acetamide | 0.1333 |
| 6 | 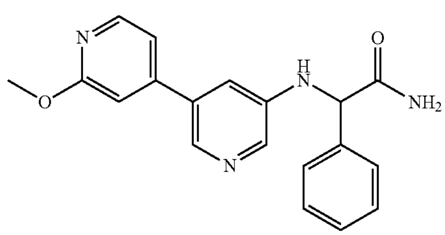 [SMILES: COc1cc(-c2cncc(NC(C(N)=O)c3ccccc3)c2)ccn1] | 2-(2'-Methoxy-[3,4']bipyridinyl-5-ylamino)-2-phenyl-acetamide | 2.1717 |
| 7 | 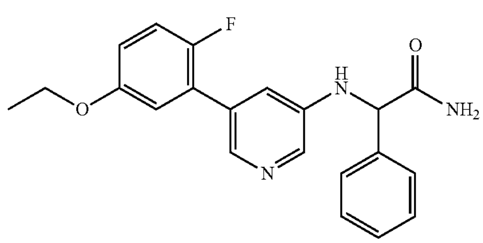 [SMILES: CCOc1ccc(F)c(-c2cncc(NC(C(N)=O)c3ccccc3)c2)c1] | 2-[5-(5-Ethoxy-2-fluoro-phenyl)-pyridin-3-ylamino]-2-phenyl-acetamide | 1.0999 |
| 8 | 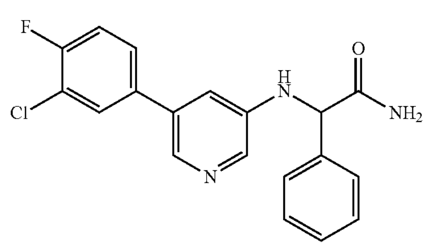 [SMILES: NC(=O)C(Nc1cncc(-c2ccc(F)c(Cl)c2)c1)c1ccccc1] | 2-[5-(3-Chloro-4-fluoro-phenyl)-pyridin-3-ylamino]-2-phenyl-acetamide | 2.3439 |

TABLE 1-continued

Structure, name and activity data of particular compounds

| Example No. | Structure | Name | IC$_{50}$ (μM) |
|---|---|---|---|
| 9 | 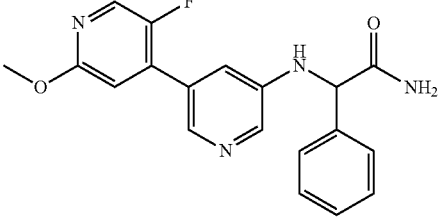 | 2-(5'-Fluoro-2'-methoxy-[3,4']bipyridinyl-5-ylamino)-2-phenyl-acetamide | 1.1538 |
| 10 | 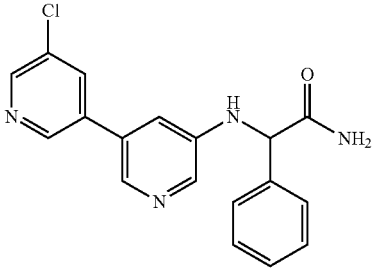 [SMILES: NC(=O)C(Nc1cncc(-c2cncc(Cl)c2)c1)c1ccccc1] | 2-(5'-Chloro-[3,3']bipyridinyl-5-ylamino)-2-phenyl-acetamide | 1.3928 |
| 11 | 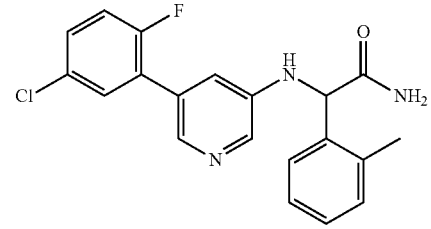 [SMILES: Cc1ccccc1C(Nc1cncc(-c2cc(Cl)ccc2F)c1)C(N)=O] | 2-[5-(5-Chloro-2-fluoro-phenyl)-pyridin-3-ylamino]-2-o-tolyl-acetamide | 0.0359 |
| 12 | 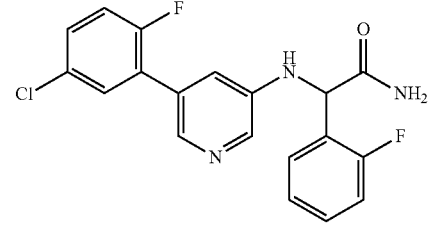 [SMILES: NC(=O)C(Nc1cncc(-c2cc(Cl)ccc2F)c1)c1ccccc1F] | 2-[5-(5-Chloro-2-fluoro-phenyl)-pyridin-3-ylamino]-2-(2-fluoro-phenyl)-acetamide | 0.0385 |
| 13 | 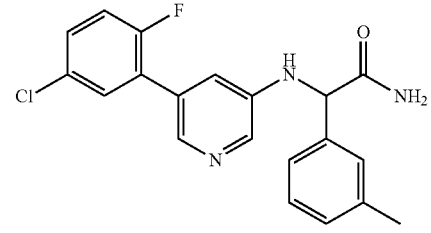 [SMILES: Cc1cccc(C(Nc2cncc(-c3cc(Cl)ccc3F)c2)C(N)=O)c1] | 2-[5-(5-Chloro-2-fluoro-phenyl)-pyridin-3-ylamino]-2-m-tolyl-acetamide | 0.5663 |
| 14 | 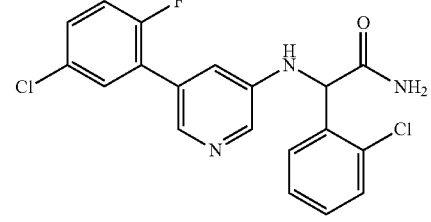 | 2-[5-(5-Chloro-2-fluoro-phenyl)-pyridin-3-ylamino]-2-(2-chloro-phenyl)-acetamide | 0.011 |

TABLE 1-continued

Structure, name and activity data of particular compounds

| Example No. | Structure | Name | IC$_{50}$ (μM) |
|---|---|---|---|
| 15 | 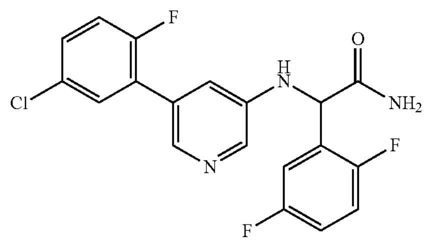 [SMILES: NC(=O)C(Nc1cncc(-c2cc(Cl)ccc2F)c1)c1cc(F)ccc1F] | 2-[5-(5-Chloro-2-fluoro-phenyl)-pyridin-3-ylamino]-2-(2,5-difluoro-phenyl)-acetamide | 0.1231 |
| 16 | 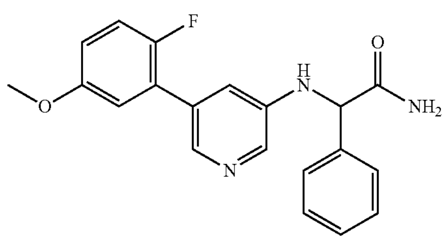 [SMILES: COc1ccc(F)c(-c2cncc(NC(C(N)=O)c3ccccc3)c2)c1] | 2-[5-(2-Fluoro-5-methoxy-phenyl)-pyridin-3-ylamino]-2-phenyl-acetamide | 0.2643 |
| 17 | 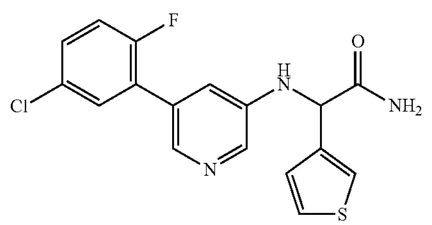 [SMILES: NC(=O)C(Nc1cncc(-c2cc(Cl)ccc2F)c1)c1ccsc1] | 2-[5-(5-Chloro-2-fluoro-phenyl)-pyridin-3-ylamino]-2-thiophen-3-yl-acetamide | 0.0542 |
| 18 | 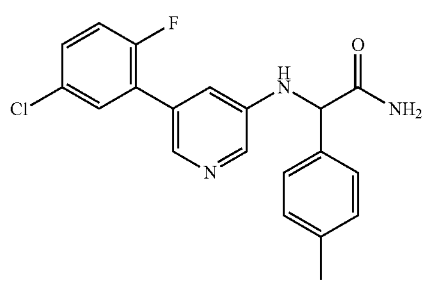 [SMILES: Cc1ccc(C(Nc2cncc(-c3cc(Cl)ccc3F)c2)C(N)=O)cc1] | 2-[5-(5-Chloro-2-fluoro-phenyl)-pyridin-3-ylamino]-2-p-tolyl-acetamide | 0.2401 |
| 19 | 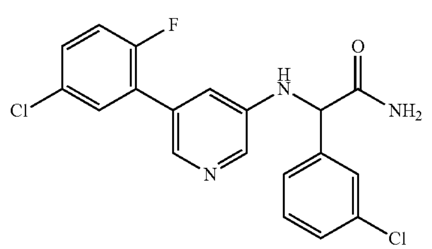 [SMILES: NC(=O)C(Nc1cncc(-c2cc(Cl)ccc2F)c1)c1cccc(Cl)c1] | 2-[5-(5-Chloro-2-fluoro-phenyl)-pyridin-3-ylamino]-2-(3-chloro-phenyl)-acetamide | 0.4324 |
| 20 | 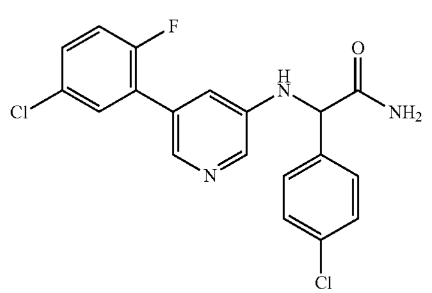 [SMILES: NC(=O)C(Nc1cncc(-c2cc(Cl)ccc2F)c1)c1ccc(Cl)cc1] | 2-[5-(5-Chloro-2-fluoro-phenyl)-pyridin-3-ylamino]-2-(4-chloro-phenyl)-acetamide | 1.0757 |

TABLE 1-continued

Structure, name and activity data of particular compounds

| Example No. | Structure | Name | $IC_{50}$ (μM) |
|---|---|---|---|
| 21 | 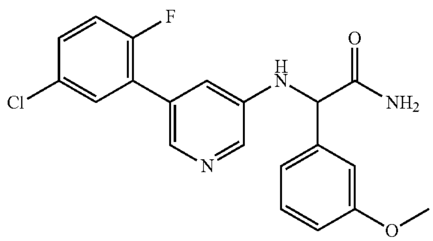 [SMILES: COc1cccc(C(Nc2cncc(-c3cc(Cl)ccc3F)c2)C(N)=O)c1] | 2-[5-(5-Chloro-2-fluoro-phenyl)-pyridin-3-ylamino]-2-(3-methoxy-phenyl)-acetamide | 0.1005 |
| 22 | 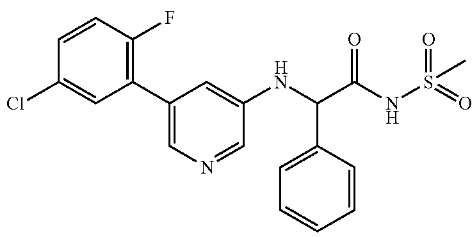 [SMILES: CS(=O)(=O)NC(=O)C(Nc1cncc(-c2cc(Cl)ccc2F)c1)c1ccccc1] | N-{2-[5-(5-Chloro-2-fluoro-phenyl)-pyridin-3-ylamino]-2-phenyl-acetyl}-methanesulfonamide | 7.7375 |
| 23 | 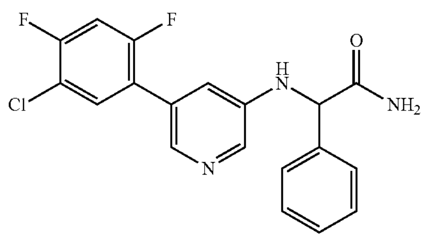 [SMILES: NC(=O)C(Nc1cncc(-c2cc(Cl)c(F)cc2F)c1)c1ccccc1] | 2-[5-(5-Chloro-2,4-difluoro-phenyl)-pyridin-3-ylamino]-2-phenyl-acetamide | 0.7207 |
| 24 | 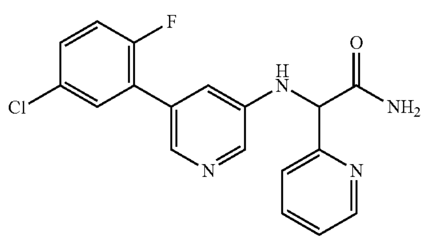 [SMILES: NC(=O)C(Nc1cncc(-c2cc(Cl)ccc2F)c1)c1ccccn1] | 2-[5-(5-Chloro-2-fluoro-phenyl)-pyridin-3-ylamino]-2-pyridin-2-yl-acetamide | 2.1078 |
| 25 | 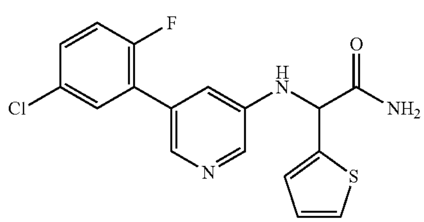 [SMILES: NC(=O)C(Nc1cncc(-c2cc(Cl)ccc2F)c1)c1cccs1] | 2-[5-(5-Chloro-2-fluoro-phenyl)-pyridin-3-ylamino]-2-thiophen-2-yl-acetamide | 0.0854 |
| 26 | 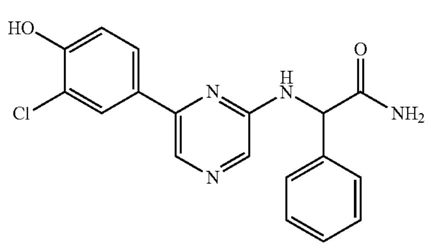 [SMILES: NC(=O)C(Nc1cncc(-c2ccc(O)c(Cl)c2)n1)c1ccccc1] | 2-[6-(3-Chloro-4-hydroxy-phenyl)-pyrazin-2-ylamino]-2-phenyl-acetamide | 0.0048 |

TABLE 1-continued

Structure, name and activity data of particular compounds

| Example No. | Structure | Name | IC$_{50}$ (μM) |
|---|---|---|---|
| 27 | 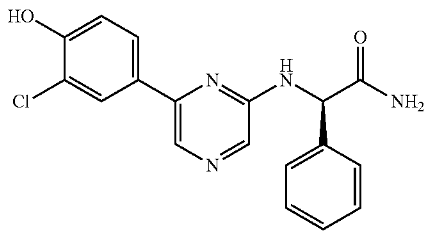 [SMILES: NC(=O)[C@H](Nc1cncc(-c2ccc(O)c(Cl)c2)n1)c1ccccc1] | (R)-2-[6-(3-Chloro-4-hydroxy-phenyl)-pyrazin-2-ylamino]-2-phenyl-acetamide | 0.0028 |
| 28 | 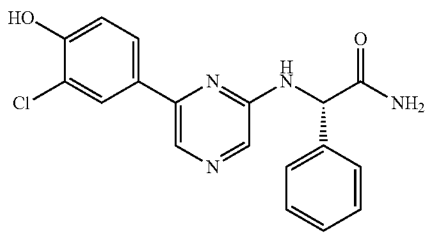 [SMILES: NC(=O)[C@@H](Nc1cncc(-c2ccc(O)c(Cl)c2)n1)c1ccccc1] | (S)-2-[6-(3-Chloro-4-hydroxy-phenyl)-pyrazin-2-ylamino]-2-phenyl-acetamide | 0.0329 |
| 29 | 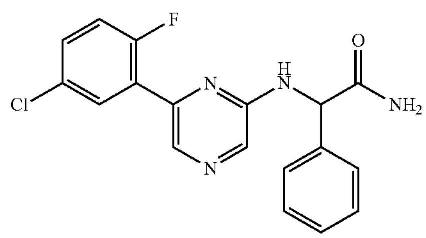 | 2-[6-(5-Chloro-2-fluoro-phenyl)-pyrazin-2-ylamino]-2-phenyl-acetamide | 0.1234 |
| 30 | 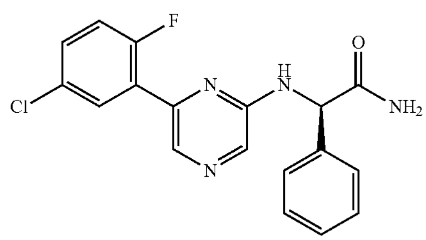 [SMILES: NC(=O)C(Nc1cncc(-c2cc(Cl)ccc2F)n1)c1ccccc1] | (R)-2-[6-(5-Chloro-2-fluoro-phenyl)-pyrazin-2-ylamino]-2-phenyl-aceamide | 0.0547 |
| 31 | 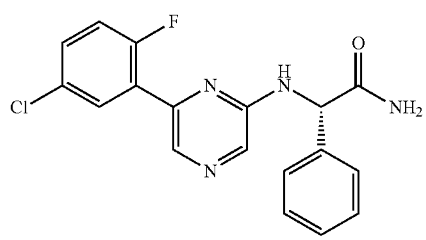 [SMILES: NC(=O)[C@@H](Nc1cncc(-c2cc(Cl)ccc2F)n1)c1ccccc1] | (S)-2-[6-(5-Chloro-2-fluoro-phenyl)-pyrazin-2-ylamino]-2-phenyl-acetamide | 0.8277 |
| 32 | 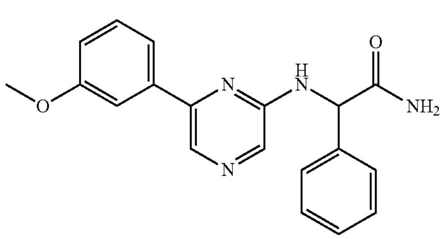 [SMILES: COc1cccc(-c2cncc(NC(C(N)=O)c3ccccc3)n2)c1] | 2-[6-(3-Methoxy-phenyl)-pyrazin-2-ylamino]-2-phenyl-acetamide | 0.4298 |

TABLE 1-continued

Structure, name and activity data of particular compounds

| Example No. | Structure | Name | IC$_{50}$ (μM) |
|---|---|---|---|
| 33 | 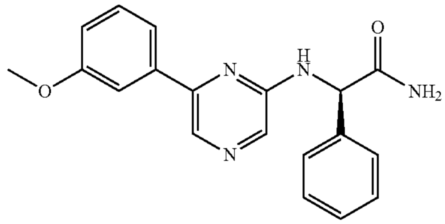 [SMILES: COc1cccc(-c2cncc(N[C@@H](C(N)=O)c3ccccc3)n2)c1] | (R)-2-[6-(3-Methoxy-phenyl)-pyrazin-2-ylamino]-2-phenyl-acetamide | 0.5665 |

TABLE 2

NMR and MS data of particular compounds

| Example No. | $^1$H NMR Data | MS obsd. (ESI$^+$) [(M + H)$^+$] |
|---|---|---|
| 1 | $^1$H NMR (METHANOL-d$_4$): δ 7.92-8.11 (m, 2H), 7.58 (d, 2H), 7.32-7.49 (m, 5H), 7.17-7.30 (m, 2H), 5.04 (s, 1H) | 356.1 |
| 2 | $^1$H NMR (METHANOL-d$_4$): δ 8.03 (s, 2H), 7.49-7.64 (m, 3H), 7.31-7.47 (m, 4H), 7.23 (s, 1H), 6.96-7.06 (m, 1H), 5.07 (s, 1H) | 354.0 |
| 3 | $^1$H NMR (METHANOL-d$_4$): δ 7.82-8.24 (m, 2H), 7.50-7.67 (m, 3H), 7.34-7.49 (m, 5H), 7.03 (d, 1H), 5.13 (s, 1H) | 354.0 |
| 4 | $^1$H NMR (METHANOL-d$_4$): δ 7.86-8.09 (m, 2H), 7.59 (d, 2H), 7.51 (d, 1H), 7.29-7.46 (m, 4H), 7.20 (s, 1H), 7.00 (d, 1H), 5.06 (s, 1H) | 354.0 |
| 5 | $^1$H NMR (METHANOL-d$_4$): δ 8.42 (d, 1H), 8.31 (s, 1 H), 8.10 (d, 1H), 7.82 (d, 1H), 7.58 (d, 2H), 7.45-7.32 (m, 4 H), 7.00 (t, 1 H), 5.03 (s, 1 H), 2.28-2.19 (m, 3 H) | 319.2 |
| 6 | $^1$H NMR (METHANOL-d$_4$): δ 8.20 (d, 1H), 8.13 (d, 1H), 8.07 (d, 1H), 7.59 (d, 2H), 7.33-7.45 (m, 3H), 7.31 (br. s., 1H), 7.17 (d, 1H), 6.99 (s, 1H), 5.08 (s, 1H), 3.96 (s, 3H) | 335.2 |
| 7 | $^1$H NMR (DMSO-d$_6$): δ 8.07 (d, 1H), 7.96 (s, 1H), 7.75 (br. s., 1H), 7.56 (d, 2H), 7.41-7.33 (m, 2H), 7.32-7.19 (m, 3H), 7.12 (br. s., 1H), 6.99-6.90 (m, 2H), 6.61 (d, 1H), 5.06 (d, 1H), 4.04 (q, 2H), 1.34 (t, 3 H) | 366.2 |
| 8 | $^1$H NMR (DMSO-d$_6$): δ 8.09 (d, 1H), 8.05 (d, 1H), 7.79 (dd, 1H), 7.73 (br. s., 1H), 7.63-7.49 (m, 4 H), 7.41-7.34 (m, 2 H), 7.33-7.20 (m, 3 H), 6.60 (d, 1 H), 5.13 (d, 1 H) | 356.1 |
| 9 | $^1$H NMR (DMSO-d$_6$): δ 8.25 (d, 1H), 8.14 (d, 1H), 8.02 (s, 1H), 7.73 (br. s., 1H), 7.55 (d, 2H), 7.34-7.40 (m, 2H), 7.24-7.32 (m, 2H), 7.19 (br. s., 1H), 6.94 (d, 1H), 6.72 (d, 1H), 5.08 (d, 1H), 3.88 (s, 3H) | 353.2 |
| 10 | $^1$H NMR (METHANOL-d$_4$): δ 8.68 (d, 1H), 8.59 (d, 1H), 8.12 (d, 1H), 8.07-8.10 (m, 2H), 7.59 (d, 2H), 7.33-7.44 (m, 3H), 7.29 (t, 1H), 5.11 (s, 1H) | 339.2 |
| 11 | $^1$H NMR (METHANOL-d$_4$): δ 7.95-8.11 (m, 2H), 7.49 (s, 3H), 7.12-7.33 (m, 5H), 5.18 (s, 1H), 2.46 (s, 2H) | 370.2 |
| 12 | $^1$H NMR (METHANOL-d$_4$): δ 7.97-8.11 (m, 2H), 7.53-7.62 (m, 1H), 7.34-7.51 (m, 3H), 7.23 (d, 4H), 5.40 (s, 1H) | 374.1 |
| 13 | $^1$H NMR (METHANOL-d$_4$): δ 7.94-8.08 (m, 2H), 7.32-7.49 (m, 4H), 7.12-7.32 (m, 4H), 4.99 (s, 1H), 2.37 (s, 3H) | 370.2 |
| 14 | $^1$H NMR (METHANOL-d$_4$): δ 7.97-8.09 (m, 2H), 7.55-7.65 (m, 1H), 7.40-7.54 (m, 3H), 7.31-7.39 (m, 2H), 7.18-7.29 (m, 2H), 5.52 (s, 1H) | 390.1 |
| 15 | $^1$H NMR (METHANOL-d$_4$): δ 7.98-8.11 (m, 2H), 7.48 (dd, 1H), 7.42 (ddd, 1H), 7.33 (ddd, 1H), 7.17-7.28 (m, 3H), 7.07-7.16 (m, 1H), 5.42 (s, 1H) | 392.2 |
| 16 | $^1$H NMR (DMSO-d$_6$): δ 8.06 (d, 1 H), 7.97 (s, 1 H), 7.75 (br. s., 1 H), 7.55 (d, 2 H), 7.40-7.34 (m, 2 H), 7.32-7.21 (m, 3 H), 7.14 (br. s., 1 H), 7.01-6.92 (m, 2 H), 6.64 (d, 1 H), 5.06 (d, 1 H), 3.78 (s, 3 H) | 352.2 |
| 17 | $^1$H NMR (METHANOL-d$_4$): δ 8.04 (d, 2H), 7.63-7.70 (m, 1H), 7.52-7.61 (m, 2H), 7.38-7.52 (m, 2H), 7.19-7.31 (m, 2H), 5.18 (s, 1H) | 362.1 |
| 18 | $^1$H NMR (METHANOL-d$_4$): δ 7.90-8.10 (m, 2H), 7.35-7.52 (m, 4H), 7.22 (d, 4H), 4.99 (s, 1H), 2.35 (s, 3H) | 370.2 |
| 19 | $^1$H NMR (METHANOL-d$_4$): δ 7.95-8.09 (m, 2H), 7.63 (s, 1H), 7.30-7.55 (m, 5H), 7.16-7.29 (m, 2H), 5.08 (s, 1H) | 390.1 |
| 20 | $^1$H NMR (METHANOL-d$_4$): δ 7.94-8.10 (m, 2H), 7.57 (d, 2H), 7.36-7.51 (m, 4H), 7.22 (d, 2H), 5.07 (s, 1H) | 390.1 |
| 21 | $^1$H NMR (METHANOL-d$_4$): δ 7.95-8.09 (m, 2H), 7.38-7.48 (m, 2H), 7.28-7.35 (m, 2H), 7.21 (s, 2H), 7.12-7.18 (m, 2H), 6.85-6.96 (m, 1H), 5.02 (s, 1H), 3.81 (s, 3H) | 386.2 |
| 22 | $^1$H NMR (DMSO-d$_6$): δ 8.12 (br. s., 1 H), 8.03 (br. s., 1 H), 7.61-7.50 (m, 4 H), 7.47-7.34 (m, 4 H), 7.18 (br. s., 1 H), 7.00-6.91 (m, 1 H), 5.28 (d, 1 H), 3.23 (s, 3 H) | 434.2 |
| 23 | $^1$H NMR (DMSO-d$_6$): δ 8.09 (d, 1 H), 7.94 (s, 1 H), 7.79-7.72 (m, 2 H), 7.68 (t, 1 H), 7.55 (d, 2 H), 7.40-7.33 (m, 2 H), 7.33-7.24 (m, 2 H), 7.12 (br. s., 1 H), 6.67 (d, 1 H), 5.07 (d, 1 H) | 374.1 |
| 24 | $^1$H NMR (METHANOL-d$_4$): δ 8.62 (d, 1H), 7.97-8.12 (m, 2H), 7.84 (d, 1H), 7.65 (d, 1H), 7.32-7.52 (m, 3H), 7.23 (d, 2H), 5.22 (s, 1H) | 357.1 |
| 25 | $^1$H NMR (METHANOL-d$_4$): δ 7.96-8.13 (m, 2H), 7.36-7.53 (m, 3H), 7.20-7.34 (m, 3H), 7.04 (dd, 1H), 5.39 (s, 1H) | 362.1 |
| 26 | $^1$H NMR (METHANOL-d$_4$): δ 7.86 (s, 1H), 7.58-7.74 (m, 2H), 7.46 (d, 1H), 7.20 (d, 2H), 6.87-7.06 (m, 3H), 6.59-6.71 (m, 1H) | 355.1 |
| 27 | $^1$H NMR (METHANOL-d$_4$): δ 8.15-8.28 (m, 1H), 8.08 (br. s., 1H), 7.94 (br. s., 1H), 7.85 (d, 1H), 7.62 (d, 2H), 7.31-7.50 (m, 3H), 7.00 (d, 1H), 5.40-5.57 (m, 1H) | 355.1 |
| 28 | $^1$H NMR (METHANOL-d$_4$): δ 8.25-8.35 (m, 1H), 8.08 (s, 2H), 7.62 (d, 2H), 7.43 (t, 4H), 7.18-7.30 (m, 1H), 5.48 (s, 1H) | 355.1 |
| 29 | $^1$H NMR (METHANOL-d$_4$): δ 8.25-8.33 (m, 1H), 8.08 (s, 2H), 7.62 (d, 2H), 7.31-7.48 (m, 4H), 7.24 (s, 1H), 5.48 (s, 1H) | 357.0 |
| 30 | $^1$H NMR (METHANOL-d$_4$): δ 8.24-8.35 (m, 1H), 7.99-8.16 (m, 2H), 7.62 (d, 2H), 7.43 (t, 4H), 7.24 (dd, 1H), 5.48 (s, 1H) | 357.0 |

TABLE 2-continued

NMR and MS data of particular compounds

| Example No. | $^1$H NMR Data | MS obsd. (ESI$^+$) [(M + H)$^+$] |
|---|---|---|
| 31 | $^1$H NMR (METHANOL-d$_4$): δ 8.25-8.35 (m, 1H), 8.08 (s, 2H), 7.62 (d, 2H), 7.43 (t, 4H), 7.18-7.30 (m, 1H), 5.48 (s, 1H) | 357.0 |
| 32 | $^1$H NMR (METHANOL-d$_4$): δ 8.27 (s, 1H), 7.99 (s, 1H), 7.62 (d, 4H), 7.25-7.49 (m, 4H), 6.91-7.04 (m, 1H), 5.36-5.56 (m, 1H), 3.88 (s, 3H) | 335.1 |
| 33 | $^1$H NMR (METHANOL-d$_4$): δ 7.69 (br. s., 1H), 7.63 (d, 4H), 7.29-7.49 (m, 5H), 6.96-7.08 (m, 1H), 5.44-5.58 (m, 1H), 3.89 (s, 3H) | 335.1 |

TABLE 3

IC$_{50}$ on HCT116, DLD-1 or AGS of particular compounds

| Example No. | IC$_{50}$ on HCT116 (colorectal cancer) | IC$_{50}$ (μM) on DLD-1 (colorectal cancer) | IC$_{50}$ (μM) on AGS (gastric cancer) |
|---|---|---|---|
| 1 | 2.6144 | | 2.6596 |
| 3 | 0.7402 | 0.6036 | 0.5168 |

More particular compounds of formula I include the following:

(R)-2-[5-(5-chloro-2-fluoro-phenyl)-pyridin-3-ylamino]-2-phenyl-cetamide;

2-[5-(3-chloro-4-hydroxy-phenyl)-pyridin-3-ylamino]-2-phenyl-acetamide;

(R)-2-[5-(3-chloro-4-hydroxy-phenyl)-pyridin-3-ylamino]-2-phenyl-acetamide;

2-[5-(5-chloro-2-fluoro-phenyl)-pyridin-3-ylamino]-2-o-tolyl-acetamide;

2-[5-(5-chloro-2-fluoro-phenyl)-pyridin-3-ylamino]-2-(2-fluoro-phenyl)-acetamide;

2-[5-(5-chloro-2-fluoro-phenyl)-pyridin-3-ylamino]-2-(2-chloro-phenyl)-acetamide;

2-[5-(2-fluoro-5-methoxy-phenyl)-pyridin-3-ylamino]-2-phenyl-acetamide;

2-[5-(5-chloro-2-fluoro-phenyl)-pyridin-3-ylamino]-2-thiophen-3-yl-acetamide;

2-[6-(3-chloro-4-hydroxy-phenyl)-pyrazin-2-ylamino]-2-phenyl-acetamide;

(R)-2-[6-(3-chloro-4-hydroxy-phenyl)-pyrazin-2-ylamino]-2-phenyl-acetamide;

2-[6-(5-chloro-2-fluoro-phenyl)-pyrazin-2-ylamino]-2-phenyl-acetamide; and (R)-2-[6-(5-chloro-2-fluoro-phenyl)-pyrazin-2-ylamino]-2-phenyl-acetamide;

Synthesis

The compounds of the present invention can be prepared by any conventional means. Suitable processes for synthesizing these compounds as well as their starting materials are provided in the schemes below and in the examples. All substituents, in particular, R$^1$, R$^2$, A and W are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Intermediate (Scheme 1)

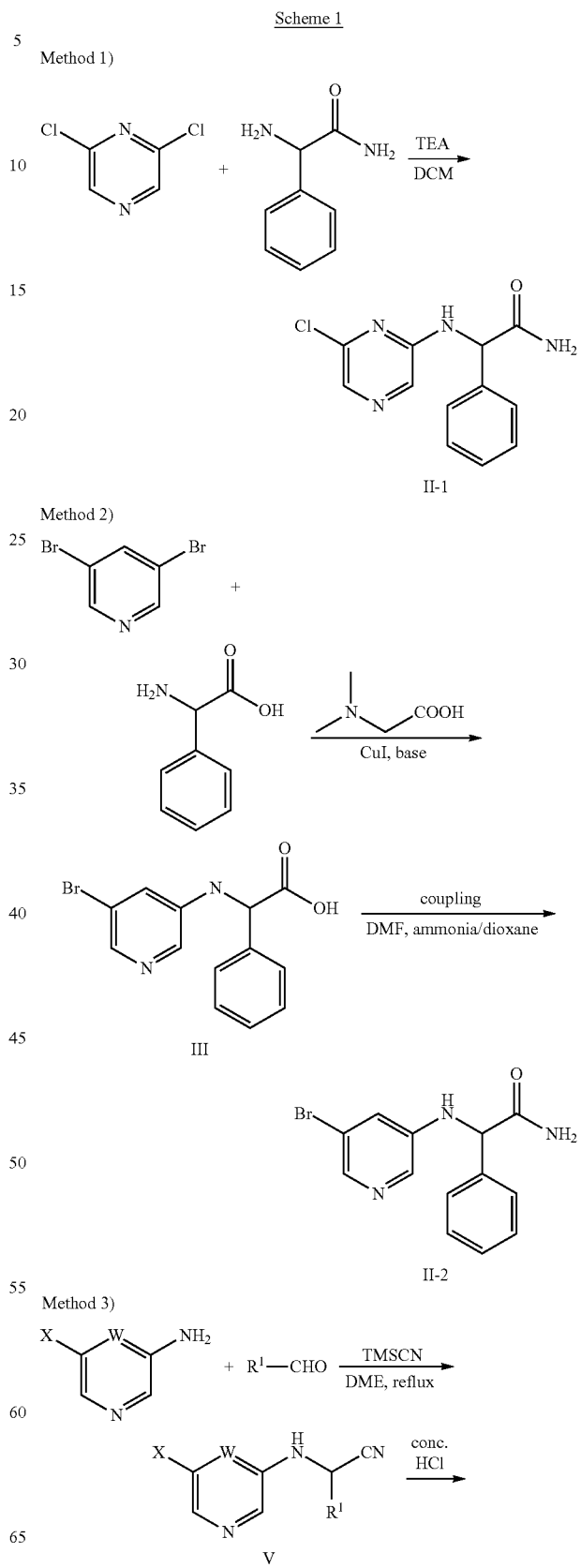

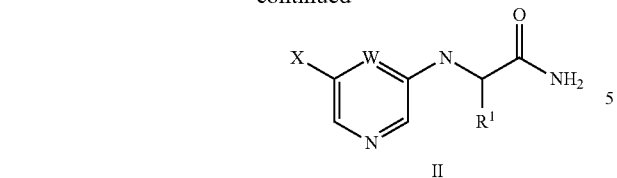

W is —N— or —CH;
X is chloro, bromo or iodo.

Intermediate II-1, I-2 and II can be prepared according to Scheme 1. By Method 1), coupling between 2,6-dichloro-pyrazine and 2-amino-2-phenyl-acetamide in the presence of TEA in DCM at room temperature for 3 days, affords intermediate II-1; or by Method 2), coupling between 3,5-dibromo-pyridine and amino-phenyl-acetic acid affords intermediate III. The reaction can be carried out in the presence of a suitable copper catalysis, a ligand such as dimethylamino-acetic acid or L-proline, and a suitable base such as $K_2CO_3$ or $Cs_2CO_3$, in a suitable solvent such as DMSO or 1,4-dioxane. Then the intermediate III reacts with ammonia/dioxane solution to afford amide I-2 under HATU in DMF. Intermediate II can be prepared by Method 3). Strecker reaction between amine IV and aldehydes affords intermediate V. Hydrolyzation of V under conc. HCl solution affords intermediate II.

General Synthetic Route for Compound Ia (Scheme 2)

General Synthetic Route for Compound Ib (Scheme 3)

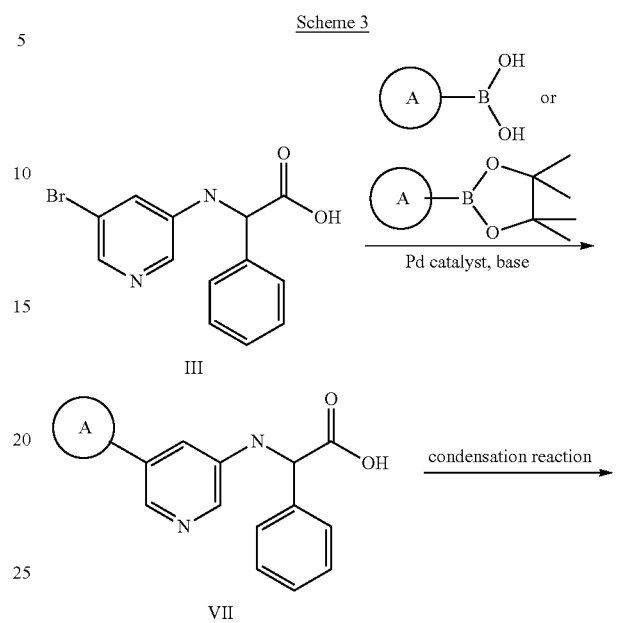

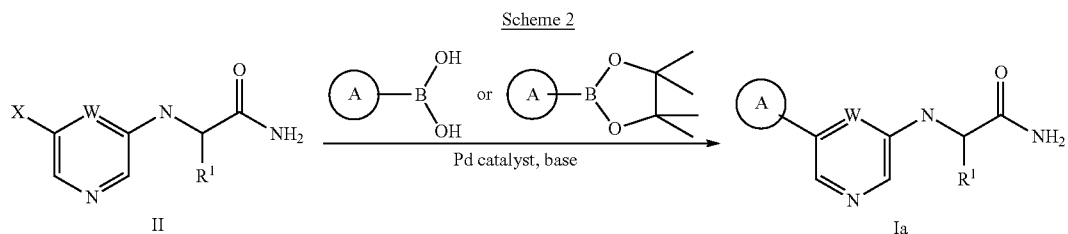

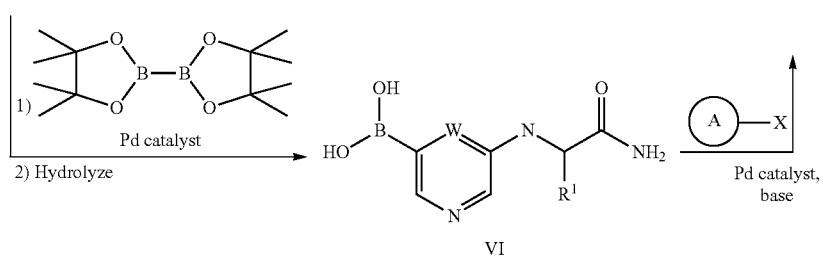

X is chloro, bromo or iodo.

The compound Ia can be prepared according to Scheme 2. One way to obtain compound Ia is that coupling between compound II and bronic acids or bronic esters affords Ia. The reaction can be carried out in the presence of a suitable Pd catalyst such as $Pd(PPh_3)_4$ or $PdCl_2(PPh_3)_2$, and a suitable base such as $K_3PO_4$, $Na_2CO_3$, $K_2CO_3$ or $Cs_2CO_3$, in a suitable solvent such as $DME/H_2O$, 1,4-dioxane/$H_2O$ or $DMF/H_2O$. Alternatively, compound Ia can also be prepared by coupling between compound II and bis(pinacolato)diboron in the presence of a suitable Pd catalyst followed by hydrolyze reaction, which affords bronic acid VI. Suzuki coupling reaction between bronic acid VI and halides affords the resulting compound Ia.

-continued

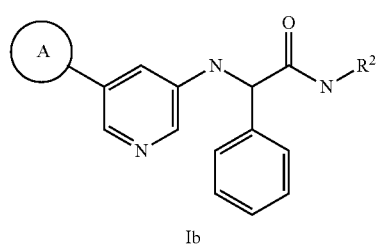

Compound Ib can be prepared according to Scheme 3. Coupling between intermediate III and bronic acids or bronic esters VII. The reaction can be carried out in the presence of a suitable Pd catalyst such as Pd(PPh$_3$)$_4$ or PdCl$_2$(PPh$_3$)$_2$, and a suitable base such as K$_3$PO$_4$, Na$_2$CO$_3$, K$_2$CO$_3$ or Cs$_2$CO$_3$. Condensation of compound VII and C$_{1-6}$alkylsulfonyl amides under the condition of HATU/DIPEA affords the resulting compound Ib.

This invention also relates to a process for the preparation of a compound of formula I comprising the reaction of (a) a compound of formula (A)

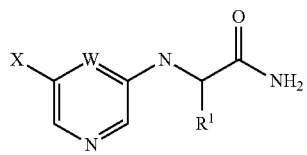

with

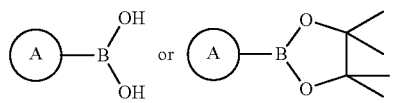

in the presence of a catalyst and a base;

(b) a compound of formula (B)

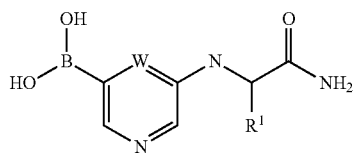

with

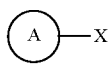

in the presence of a catalyst and a base;

(c) a compound of formula (C)

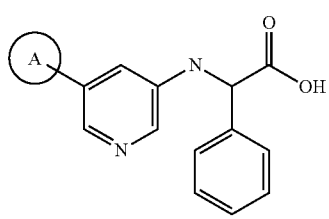

with C$_{1-6}$alkylsulfonyl amides in the presence of HATU/DIPEA;

wherein R$^1$, R$^2$, A and W are defined above unless otherwise indicated; X is chloro, bromo or iodo.

In step (a), the catalyst can be for example Pd(PPh$_3$)$_4$ or PdCl$_2$(PPh$_3$)$_2$, the base can be for example K$_3$PO$_4$, Na$_2$CO$_3$, K$_2$CO$_3$ or Cs$_2$CO$_3$;

In step (b), the catalyst can be for example Pd(PPh$_3$)$_4$, the base can be for example K$_2$CO$_3$.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but particularly ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit CDK8 activity. For example, such amount may be below the amount that is toxic to normal cells, or the mammal as a whole.

In one example, the pharmaceutically effective amount of the compound of the invention administered parenterally per dose will be in the range of about 0.1 to 50 mg/kg of patient body weight per day, with the typical initial range of compound used being about 0.3 to about 15 mg/kg/day. In another embodiment, oral unit dosage forms, such as tablets and capsules, preferably contain from about 5 mg to about 500 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 5 mg to 500 mg of the compound of the invention compounded with about 90 mg to 30 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Another embodiment includes a pharmaceutical composition comprising a compound of Formula I for use in the treatment of a hyperproliferative disease. Another embodiment includes a pharmaceutical composition comprising a compound of Formula I for use in the treatment of cancer.

Indications and Methods of Treatment

The compounds of the invention inhibit the kinase activity of protein. Accordingly, the compounds of the invention are useful for inhibiting cell proliferation and inducing cell cycle arrest and apoptosis in particular cancer cells.

Compounds of the invention are useful for inhibiting cell proliferation, inducing cell cycle arrest and apoptosis in cells that overexpress CDK8 or Cyclin C.

Alternatively, compounds of the invention are useful for inhibiting cell proliferation, inducing cell cycle arrest and apoptosis in cells in which the apoptotic pathway is disrupted or proliferation pathway is overexpressed/or immortalized, for example by deregulation of CDK8 or Cyclin C.

An embodiment of this invention includes the use of a compound for the treatment of cancer, in particular bladder, head and neck, breast, stomach, ovary, colon, lung, brain, larynx, lymphatic system, liver, skin, hematopoetic system, genitourinary tract, gastrointestinal, ovarian, prostate, gastric, bone, small-cell lung, glioma, colorectal and pancreatic cancers. A further embodiment of this invention includes the use of a compound for the treatment of gastric cancer or colorectal cancer.

Another embodiment of this invention includes the use of a compound for the preparation of a medicament for the treatment of cancer, in particular bladder, head and neck, breast, stomach, ovary, colon, lung, brain, larynx, lymphatic system, liver, skin, hematopoetic system, genitourinary tract, gastrointestinal, ovarian, prostate, gastric, bone, small-cell lung, glioma, colorectal and pancreatic cancers.

A further embodiment of this invention includes the use of a compound for the preparation of a medicament for the treatment of gastric cancer or colorectal cancer.

Another embodiment of this invention relates to a compound of formula I for the treatment of cancer, in particular bladder, head and neck, breast, stomach, ovary, colon, lung, brain, larynx, lymphatic system, liver, skin, hematopoetic system, genitourinary tract, gastrointestinal, ovarian, prostate, gastric, bone, small-cell lung, glioma, colorectal and pancreatic cancers.

A further embodiment of this invention relates to a compound of formula I for the treatment of gastric cancer or colorectal cancer.

Another embodiment includes a method of treating or preventing cancer in a mammal in need of such treatment, wherein the method comprises administering to said mammal a therapeutically effective amount of a compound of Formula I, a stereoisomer, tautomer, prodrug or pharmaceutically acceptable salt thereof. Particular cancers for treatment or prevention include bladder, head and neck, breast, stomach, ovary, colon, lung, brain, larynx, lymphatic system, liver, skin, hematopoetic system, genitourinary tract, gastrointestinal, ovarian, prostate, gastric, bone, small-cell lung, glioma, colorectal and pancreatic cancers. More particularly, the invention relates to a method of treating or preventing gastric cancer or colorectal cancer in a mammal in need of such treatment, wherein the method comprises administering to said mammal a therapeutically effective amount of a compound of Formula I, a stereoisomer, tautomer, prodrug or pharmaceutically acceptable salt thereof. Another embodiment includes a method of treating or preventing neurodegenerative disease in a mammal in need of such treatment, wherein the method comprises administering to said mammal a therapeutically effective amount of a compound of Formula I, a stereoisomer, tautomer, prodrug or pharmaceutically acceptable salt thereof. Particular neurodegenerative disease for treatment includes Alzhemers disease, parkinson's disease, Huntington's disease and Amyotrophic lateral sclerosis (ALS).

Combination Therapy

The compounds of the invention can be used in combination with small molecule inhibitors such as tyrosine kinase inhibitors, Serine/Threonine kinase inhibitors, lipid kinase inhibitors, protein-protein inhibitors, etc., cytotoxic agents, radiotherapy, antibodies and cancer vaccines for the treatment of cancer.

EXAMPLES

The invention will be more fully understood by reference to the following examples. They should not, however, be construed as limiting the scope of the invention.

Abbreviations used herein are as follows:

μL: microliter

μm: micrometer

μM: micromoles per liter aq.: aqueous

Ar: argon
BSA: bovine serum albumin
CCK-8: Cell Counting Kit-8
conc.: concentrated
DCM: dichloromethane
DIPEA: N,N-diisopropylethylamine
DME: 1,2-dimethoxyethane
DMF: dimethylformamide
DMSO-d6: deuterated dimethylsulfoxide
DTT: dithiothreitol
EA or EtOAc: ethyl acetate
EGTA: ethylene glycol tetraacetic acid
g: gram
h or hr: hour
hrs: hours
$IC_{50}$: the half maximal inhibitory concentration
HATU: 2-(7-aza-1H-benzotriazole-1-yl)-1,1,3,3-tetramethyluronium hexafluorophosphate
HCMV: human cytomegalovirus
HIV: human immunodeficiency
HSV: herpes simplex virus
HPV: human papillomavirus
HPLC: high performance liquid chromatography
LC/MS: liquid chromatography/mass spectrometry
M: molarity
MeOH: methanol
METHANOL-$d_4$: perdeuteromethanol
mg: milligram
MHz: megahertz
min: minute
mins: minutes
mL: milliliter
mM: millimoles per liter
mm: millimeter
mmol: millimole
MS (ESI): mass spectroscopy (electron spray ionization)
nM: nanomoles per liter
nm: nanometer
NMR: nuclear magnetic resonance
obsd.: observed
OD: optical density
RT: room temperature
Pd(PPh$_3$)$_4$: tetrakis(triphenylphosphine)palladium
Pd(PPh$_3$)$_2$Cl$_2$: bis(triphenylphosphine)palladium(II) chloride
PE: petroleum ether
Prep HPLC: preparative high performance liquid chromatography
rac. racemic
SFC: supercritical fluid chromatography
TEA: triethylamine
TLC: thin layer chromatography
TMSCN: trimethylsilyl cyanide
TR-FRET: time resolved-fluorescence resonance energy transfer
δ: chemical shift General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):Acidic condition: A: 0.1% formic acid in H$_2$O; B: 0.1% formic acid in acetonitrile;

Basic condition: A: 0.01% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

PREPARATIVE EXAMPLES

Example 1

Preparation of (R)-2-[5-(5-chloro-2-fluoro-phenyl)-pyridin-3-ylamino]-2-phenyl-acetamide Step 1: Preparation of 5-bromo-pyridin-3-ylamino-phenyl-acetic acid

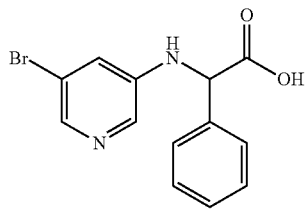 [SMILES: O=C(O)C(Nc1cncc(Br)c1)c1ccccc1]

To a solution of 3,5-dibromopyridine (19 g, 80 mmol) in DMSO (150 mL) was added 2-phenylglycine (18 g, 120 mmol), copper(I) iodide (1.52 g, 8 mmol), L-proline (1.84 g, 16 mmol) and K$_2$CO$_3$ (22 g, 160 mmol). The resulting mixture was degassed and then stirred at 90° C. for 12 hrs under an Ar atmosphere. After the reaction was completed as monitored by LC-MS, the mixture was diluted with water (500 mL) and then extracted with EtOAc. The combined organic layers were washed with water and brine, and then dried. The solvent was concentrated and the residue was purified by column chromatography (DCM/MeOH=20:1) to give 5-bromo-pyridin-3-ylamino-phenyl-acetic acid (5.6 g).

Step 2: Preparation of
2-(5-bromo-pyridin-3-ylamino)-2-phenyl-acetamide

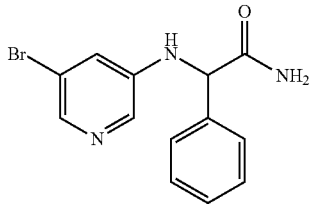

To a solution of 5-bromo-pyridin-3-ylamino-2-phenyl-acetic acid (2.8 g, 9.15 mmol) in anhydrous DMF (30 mL) was added 36.6 mL NH$_3$ solution (0.5 M in 1,4-dioxane) and triethylamine (1.85 g, 18.3 mmol). The resulting mixture was stirred for 30 mins, after that, HATU (7.0 g, 18.3 mmol) was added in batches and then the mixture was stirred overnight at room temperature. The mixture was diluted with water (200 mL) and then extracted with EtOAc (2×100 mL). The combined organic layers were washed with water and brine, and then dried. The solvent was concentrated and the residue was purified by column chromatography (DCM/MeOH=20:1) to give 2-(5-bromo-pyridin-3-ylamino)-2-phenyl-acetamide (1.2 g).

Step 3: Preparation of (R)-2-[5-(5-chloro-2-fluoro-phenyl)-pyridin-3-ylamino]-2-phenyl-acetamide To a solution of 2-(5-bromo-pyridin-3-ylamino)-2-phenyl-acetamide (150 mg, 0.5 mmol) in DME-H$_2$O (5:1, 6 mL) was added Pd(PPh$_3$)$_4$ (115 mg, 0.1 mmol), K$_2$CO$_3$ (138 mg, 1.0 mmol) and 5-chloro-2-fluorophenylboronic acid (105 mg, 0.6 mmol). The resulting mixture was degassed and then stirred for 10 hrs at 80° C. under an Ar atmosphere. After cooling, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-phenyl-acetamide (25 mg).

Separation of the two enantiomers from 2-[5-(5-chloro-2-fluoro-phenyl)-pyridin-3-ylamino]-2-phenyl-acetamide (25 mg) was conducted by chiral SFC to provide chiral (R)-2-[5-(5-chloro-2-fluoro-phenyl)-pyridin-3-ylamino]-2-phenyl-acetamide (10 mg).

Example 2

Preparation of 2-[5-(3-chloro-4-hydroxy-phenyl)-pyridin-3-ylamino]-2-phenyl-acetamide Under an Ar atmosphere, a mixture of 2-(5-bromo-pyridin-3-ylamino)-2-phenyl-acetamide (152 mg, 0.5 mmol), 3-chloro-4-hydroxyphenylboronic acid pinacol ester (152 mg, 0.6 mmol), Pd(PPh$_3$)$_2$Cl$_2$ (35 mg, 0.05 mmol), 2-(di-cyclohexyphosphino)biphenyl (35 mg, 0.1 mmol) and Na$_2$CO$_3$ (106 mg, 1.0 mmol) in DME-H$_2$O (5:1, 3 mL) was exposed to microwave irradiation at 130° C. for 30 mins, then the reaction mixture was concentrated in vacuo. The residue was partitioned between EtOAc and brine. The aqueous layer was separated and extracted with EtOAc. The combined organic layers were concentrated and the residue was purified by Prep-HPLC to give 2-[5-(3-chloro-4-hydroxy-phenyl)-pyridin-3-ylamino]-2-phenyl-acetamide (45 mg).

Example 3

Preparation of (R)-2-[5-(3-chloro-4-hydroxy-phenyl)-pyridin-3-ylamino]-2-phenyl-acetamide Separation of the two enantiomers from 2-[5-(3-chloro-4-hydroxy-phenyl)-pyridin-3-ylamino]-2-phenyl-acetamide (45 mg) was conducted by chiral SFC to provide chiral (R)-2-[5-(3-chloro-4-hydroxy-phenyl)-pyridin-3-ylamino]-2-phenyl-acetamide (10 mg).

Example 4

Preparation of (S)-2-[5-(3-chloro-4-hydroxy-phenyl)-pyridin-3-ylamino]-2-phenyl-acetamide Separation of the two enantiomers from 2-[5-(3-chloro-4-hydroxy-phenyl)-pyridin-3-ylamino]-2-phenyl-acetamide (45 mg) was conducted by chiral SFC to provide chiral (S)-2-[5-(3-chloro-4-hydroxy-phenyl)-pyridin-3-ylamino]-2-phenyl-acetamide (8 mg).

Example 5

Preparation of 2-(4'-methyl-[3,3']bipyridinyl-5-ylamino)-2-phenyl-acetamide

Under an Ar atmosphere, a mixture of 2-(5-bromo-pyridin-3-ylamino)-2-phenyl-acetamide (200 mg, 0.65 mmol), (4-methyl-3-pyridinyl)-boronic acid (90 mg, 0.65 mmol), tetrakis(triphenylphosphine)palladium (40 mg) and potassium carbonate (180 mg, 1.3 mmol) in DME-H$_2$O (5:1, 4.5 mL) was heated at microwave to 90° C. for 40 mins. Then, the residue was partitioned between EtOAc and brine. The aqueous layer was separated and extracted with EtOAc. The combined organic layers were concentrated and the residue was purified by Prep-HPLC to give 2-(4'-methyl-[3,3']bipyridinyl-5-ylamino)-2-phenyl-acetamide (30 mg).

Example 6

Preparation of 2-(2'-methoxy-[3,4']bipyridinyl-5-ylamino)-2-phenyl-acetamide

Under an Ar atmosphere, a mixture of 2-(5-bromo-pyridin-3-ylamino)-2-phenyl-acetamide (60 mg, 0.197 mmol), 2-methoxypyridne-4-boronic acid (39 mg, 0.256 mmol), Tetrakis(triphenylphosphine)palladium (11 mg, 0.0098 mmol) and K$_2$CO$_3$ (81 mg, 0.59 mmol) in DME-H2O (5:1, 2 mL) was exposed to microwave irradiation at 95° C. for 1 hr, then concentrated in vacuo. The residue was partitioned between ethyl acetate and brine. The aqueous layer was separated and extracted with ethyl acetate. The combined organic layers were concentrated and the residue was purified by Prep-HPLC to give 2-(2'-methoxy-[3,4']bipyridinyl-5-ylamino)-2-phenyl-acetamide (14 mg).

Example 7

Preparation of 2-[5-(5-ethoxy-2-fluoro-phenyl)-pyridin-3-ylamino]-2-phenyl-acetamide 2-(5-Bromo-pyridin-3-ylamino)-2-phenyl-acetamide (60 mg, 0.2 mmol), 5-ethoxy-2-fluorophenylboronic acid (48 mg, 0.26 mmol), tetrakis(triphenylphosphine)-palladium (11 mg, 0.01 mmol) and potassium carbonate (81 mg, 0.6 mmol) were added into a 10 mL microwave vial containing a magnetic stirrer bar, followed by DME (1 mL) and H₂O (0.2 mL). The vessel was sealed with a cap under an argon atmosphere, and then the resulting mixture was heated to 90° C. for 40 mins under microwave. The mixture was cooled to room temperature and diluted with water (5 mL), extracted with ethyl acetate (10 mL×3), the combined organic layers were washed with brine (10 mL), dried over anhydrous sodium sulfate, concentrated in vacuo to give crude product. The crude product was purified by C-18 reversed phase HPLC column to give desired 2-[5-(5-ethoxy-2-fluoro-phenyl)-pyridin-3-ylamino]-2-phenyl-acetamide (20 mg) as a white solid.

Example 8

Preparation of 2-[5-(3-chloro-4-fluoro-phenyl)-pyridin-3-ylamino]-2-phenyl-acetamide 2-(5-Bromo-pyridin-3-ylamino)-2-phenyl-acetamide (60 mg, 0.2 mmol), 3-chloro-4-fluorophenylboronic acid (45 mg, 0.26 mmol), tetrakis(triphenylphosphine) palladium (11 mg, 0.01 mmol) and potassium carbonate (81 mg, 0.6 mmol) were added into a 10 mL microwave vial containing a magnetic stirrer bar, followed by DME (1 mL) and H₂O (0.2 mL). The vessel was sealed with a cap under an argon atmosphere, then the resulting mixture was heated to 90° C. for 40 mins under microwave. The mixture was cooled to room temperature and diluted with water (5 mL), extracted with ethyl acetate (10 mL×3), the combined organic layers were washed with brine (10 mL), dried over anhydrous sodium sulfate, concentrated in vacuo to give crude product after purified by C-18 reversed phase HPLC column to give desired 2-[5-(3-chloro-4-fluoro-phenyl)-pyridin-3-ylamino]-2-phenyl-acetamide (25 mg) as a white solid.

Example 9

Preparation of 2-(5'-fluoro-2'-methoxy-[3,4']bipyridinyl-5-ylamino)-2-phenyl-acetamide Under an Ar atmosphere, a mixture of 2-(5-bromo-pyridin-3-ylamino)-2-phenyl-acetamide (200 mg, 0.656 mmol), (5-fluoro-2-methoxypyridin-4-yl)boronic acid (336 mg, 1.96 mmol), Pd(PPh₃)₄ (76 mg, 0.066 mmol) and K₂CO₃ (542 mg, 3.93 mmol) in DME-H₂O (5:1, 4 mL) was exposed to microwave irradiation at 105° C. for 2 hrs, then the mixture was concentrated in vacuo. The residue was partitioned between EtOAc and brine. The aqueous layer was separated and extracted with EtOAc. The combined organic layers were concentrated and the residue was purified by Prep-HPLC to give 2-(5'-fluoro-2'-methoxy-[3,4']bipyridinyl-5-ylamino)-2-phenyl-acetamid (35 mg).

Example 10

Preparation of 2-(5'-chloro-[3,3']bipyridinyl-5-ylamino)-2-phenyl-acetamide

Under an Ar atmosphere, a mixture of 2-(5-bromo-pyridin-3-ylamino)-2-phenyl-acetamide (100 mg, 0.328 mmol), (5-chloropyridin-3-yl)boronic acid (62 mg, 0.393 mmol), Pd(PPh₃)₄ (19 mg, 0.016 mmol) and K₂CO₃ (136 mg, 0.98 mmol) in DME-H₂O (5:1, 2 mL) was exposed to microwave irradiation at 100° C. for 50 mins, then the mixture was concentrated in vacuo. The residue was partitioned between EtOAc and brine. The aqueous layer was separated and extracted with EtOAc. The combined organic layers were concentrated and the residue was purified by Prep-HPLC to give 2-(5'-chloro-[3,3']bipyridinyl-5-ylamino)-2-phenyl-acetamide (45 mg).

Example 11

Preparation of 2-[5-(5-fhloro-2-fluoro-phenyl)-pyridin-3-ylamino]-2-o-tolyl-acetamide Step 1: Preparation of 5-bromo-pyridin-3-ylamino-o-tolyl-acetonitrile

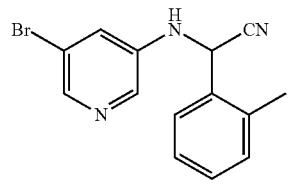 [SMILES: Cc1ccccc1C(C#N)Nc1cncc(Br)c1]

To a solution of 5-bromo-pyridin-3-ylamine (7.00 g, 40.5 mmol) and 2-methyl-benzaldehy (5.83 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give 5-bromo-pyridin-3-ylamino-o-tolyl-acetonitrile (10.03 g).

Step 2: Preparation of 2-(5-bromo-pyridin-3-ylamino)-2-o-tolyl-acetamide

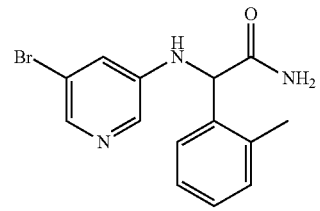

A mixture of 5-bromo-pyridin-3-ylamino-o-tolyl-acetonitrile (2.00 g, 6.6 mmol) and conc. HCl aq (4 mL) was stirred at 40° C. for 1 h. Water (200 mL) was added to the reaction mixture. The mixture was washed with EtOAc (50 mL×2). Then the aqueous solution was alkalized to pH=7.0-8.0 with concentrated ammonium hydroxide and extracted with EtOAc (100 mL×3). The organic layer was separated, washed with brine (100 mL), dried over Na₂SO₄, concentrated under reduced pressure to give 2-(5-bromo-pyridin-3-ylamino)-2-o-tolyl-acetamide (1.52 g).

Step 3: Preparation of 2-[5-(5-chloro-2-fluoro-phenyl)-pyridin-3-ylamino]-2-o-tolyl-acetamide To a solution of 2-(5-bromo-pyridin-3-ylamino)-2-o-tolyl-acetamide (320 mg, 1.0 mmol) in DME-H₂O (5:1, 6 mL) was added Pd(PPh₃)₄ (231 mg, 0.2 mmol), K₂CO₃ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was complete as indicated by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-o-tolyl-acetamide (65 mg).

Example 12

Preparation of 2-[5-(5-chloro-2-fluoro-phenyl)-pyridin-3-ylamino]-2-(2-fluoro-phenyl)-acetamide Step 1: Preparation of (5-bromo-pyridin-3-ylamino)-(2-fluoro-phenyl)-acetonitrile

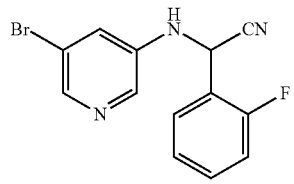 [SMILES: N#CC(Nc1cncc(Br)c1)c1ccccc1F]

To a solution of 5-bromo-pyridin-3-ylamine (7.00 g, 40.5 mmol) and 2-fluoro-benzaldehye (6.03 g, 48.6 mmol) in DME (50 mL) was added TMSCN (6.03 g, 60.8 mmol) dropwise at room temperature. The reaction mixture was refluxed for 16 hrs. After the reaction was complete as monitored by TLC, the reaction solution was concentrated. The residue was purified through Chemflash, eluted with a gradient from 0% to 40% EtOAc in petroleum ether to give (5-bromo-pyridin-3-ylamino)-(2-fluoro-phenyl)-acetonitrile (8.35 g).

Step 2: Preparation of 2-(5-bromo-pyridin-3-ylamino)-2-(2-fluoro-phenyl)-acetamide

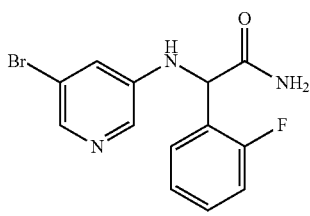

A mixture of conc. HCl (6 mL) and (5-bromo-pyridin-3-ylamino)-(2-fluoro-phenyl)-acetonitrile (3 g, 10 mmol) was stirred at 40° C. for about 1 h. Upon the completion of the reaction which was monitored by TLC, the mixture was diluted with water (200 mL) and washed with EtOAc (100 mL×2). Then the aqueous solution was alkalized to pH=7.0-8.0 with concentrated ammonium hydroxide and extracted with EtOAc (100 mL×3). The organic layer was separated, washed with brine (100 mL), dried over $Na_2SO_4$, then concentrated under reduced pressure to give 2-(5-bromo-pyridin-3-ylamino)-2-(2-fluoro-phenyl)-acetamide (1.75 g) as a yellow solid.

Step 3: Preparation of 2-[5-(5-chloro-2-fluoro-phenyl)-pyridin-3-ylamino]-2-(2-fluoro-phenyl)-acetamide To a solution of 2-(5-bromo-pyridin-3-ylamino)-2-(2-fluoro-phenyl)-acetamide (324 mg, 1.0 mmol) in DME-$H_2O$ (5:1, 6 mL) was added Pd(PPh$_3$)$_4$ (231 mg, 0.2 mmol), $K_2CO_3$ (276 mg, 2.0 mmol) and 5-chloro-2-fluorophenyl-boronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-(2-fluoro-phenyl)-acetamide (75 mg).

Example 13

Preparation of 2-[5-(5-chloro-2-fluoro-phenyl)-pyridin-3-ylamino]-2-m-tolyl-acetamide Step 1: Preparation of (5-bromo-pyridin-3-ylamino)-m-tolyl-acetonitrile

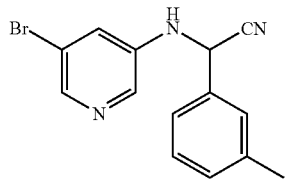 [SMILES: Cc1cccc(C(C#N)Nc2cncc(Br)c2)c1]

To a solution of 5-bromo-pyridin-3-ylamine (7.00 g, 40.5 mmol) and 3-methyl-benzaldehyde (5.83 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-m-tolyl-acetonitrile (8.52 g).

Step 2: Preparation of 2-(5-bromo-pyridin-3-ylamino)-2-m-tolyl-acetamide

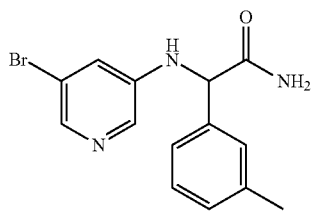 [SMILES: Cc1cccc(C(Nc2cncc(Br)c2)C(N)=O)c1]

A mixture of (5-bromo-pyridin-3-ylamino)-m-tolyl-acetonitrile (3 g, 10 mmol) in concentrated HCl (6 mL) was stirred at 40° C. for 40 mins. Upon the completion of the reaction which was monitored by TLC, the reaction solution was diluted with H2O/EA (1/1, 500 mL). The aqueous layer was separated and adjusted to pH=9 with ammonia, extracted with EtOAc (200 mL). The organic layer was concentrated in vacuo and recrystallized to give 2-(5-bromo-pyridin-3-ylamino)-2-m-tolyl-acetamide (1.2 g) as a yellow solid.

Step 3: Preparation of 2-[5-(5-chloro-2-fluoro-phenyl)-pyridin-3-ylamino]-2-m-tolyl-acetamide To a solution of 2-(5-bromo-pyridin-3-ylamino)-2-m-tolyl-acetamide (320 mg, 1.0 mmol) in DME-H$_2$O (5:1, 6 mL) was added Pd(PPh$_3$)$_4$ (231 mg, 0.2 mmol), K$_2$CO$_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give rac-2-[5-(5-chloro-2-fluoro-phenyl)-pyridin-3-ylamino]-2-m-tolyl-acetamide (80 mg).

Example 14

Preparation of 2-[5-(5-chloro-2-fluoro-phenyl)-pyridin-3-ylamino]-2-(2-chloro-phenyl)-acetamide Step 1: Preparation of (5-bromo-pyridin-3-ylamino)-(2-chloro-phenyl)-acetonitrile

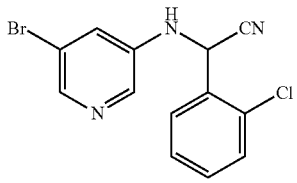 [SMILES: N#CC(Nc1cncc(Br)c1)c1ccccc1Cl]

To a solution of 5-bromo-pyridin-3-ylamine (7.00 g, 40.5 mmol) and 2-chloro-benzaldehyde (6.83 g, 48.6 mmol) in DME (50 mL) was added TMSCN (6.03 g, 60.8 mmol) dropwise at room temperature. The reaction mixture was refluxed for 16 hrs. Upon the completion of the reaction which was monitored by TLC, the reaction solution was concentrated. The residue was purified through Chemflash, eluted with a gradient from 0% to 40% EtOAc in petroleum ether to give (5-bromo-pyridin-3-ylamino)-(2-chloro-phenyl)-acetonitrile (8.12 g).

Step 2: Preparation of 2-(5-bromo-pyridin-3-ylamino)-2-(2-chloro-phenyl)-acetamide

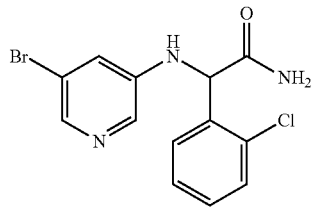 [SMILES: NC(=O)C(Nc1cncc(Br)c1)c1ccccc1Cl]

To 12 N HCl (6 mL) was added (5-bromo-pyridin-3-ylamino)-(2-chloro-phenyl)-acetonitrile (3 g, 9 mmol), the solution was stirred at 40° C. for about 1 h. Upon the completion of the reaction which was monitored by TLC, the reaction solution was diluted with H$_2$O/EA (1/1, 500 mL). The aqueous layer was separated and adjusted to pH=9 with ammonia, extracted with EtOAc (200 mL). The organic layer was concentrated in vacuo and recrystallized to give 2-(5-bromo-pyridin-3-ylamino)-2-(2-chloro-phenyl)-acetamide (1.75 g) as a yellow solid.

Step 3: Preparation of 2-[5-(5-chloro-2-fluoro-phenyl)-pyridin-3-ylamino]-2-(2-chloro-phenyl)-acetamide To a solution of 2-(5-bromo-pyridin-3-ylamino)-2-(2-chloro-phenyl)-acetamide (340 mg, 1.0 mmol) in DME-H$_2$O (5:1, 6 mL) was added Pd(PPh$_3$)$_4$ (231 mg, 0.2 mmol), K$_2$CO$_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-(2-chloro-phenyl)-acetamide (60 mg).

Example 15

Preparation of 2-[5-(5-chloro-2-fluoro-phenyl)-pyridin-3-ylamino]-2-(2,5-difluoro-phenyl)-acetamide Step 1: Preparation of (5-bromo-pyridin-3-ylamino)-(2,5-difluoro-phenyl)-acetonitrile

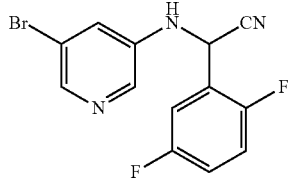 [SMILES: N#CC(Nc1cncc(Br)c1)c1cc(F)ccc1F]

To a solution of 5-bromo-pyridin-3-ylamine (7.00 g, 40.5 mmol) and 2,5-difluoro-benzaldehyde (6.91 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-(2,5-difluoro-phenyl)-acetonitrile (9.65 g).

Step 2: Preparation of 2-(5-bromo-pyridin-3-ylamino)-2-(2,5-difluoro-phenyl)-acetamide

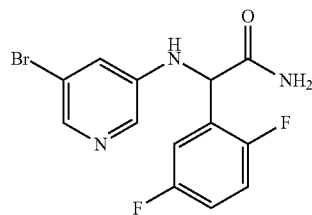 [SMILES: NC(=O)C(Nc1cncc(Br)c1)c1cc(F)ccc1F]

A mixture of (5-bromo-pyridin-3-ylamino)-(2,5-difluoro-phenyl)-acetonitrile (3.00 g, 9.3 mmol) and conc. HCl (6 mL) was stirred at 40° C. for 1 h. Water (250 mL) was added to the reaction mixture. The mixture was washed with EtOAc (100 mL×2). Then the aqueous solution was alkalized to pH=7.0-8.0 with concentrated ammonium hydroxide and extracted with EtOAc (100 mL×3). The organic layer was separated, washed with brine (100 mL), dried over $Na_2SO_4$, concentrated under reduced pressure to give 2-(5-bromo-pyridin-3-ylamino)-2-(2,5-difluoro-phenyl)-acetamide (1.15 g).

Step 3: Preparation of 2-[5-(5-chloro-2-fluoro-phenyl)-pyridin-3-ylamino]-2-(2,5-difluoro-phenyl)-acetamide To a solution of 2-(5-bromo-pyridin-3-ylamino)-2-(2,5-difluoro-phenyl)-acetamide (342 mg, 1.0 mmol) in DME-$H_2O$ (5:1, 6 mL) was added $Pd(PPh_3)_4$ (231 mg, 0.2 mmol), $K_2CO_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-(2,5-difluoro-phenyl)-acetamide (55 mg).

Example 16

Preparation of 2-[5-(2-fluoro-5-methoxy-phenyl)-pyridin-3-ylamino]-2-phenyl-acetamide 2-(5-Bromo-pyridin-3-ylamino)-2-phenyl-acetamide (60 mg, 0.2 mmol), 5-methoxy-2-fluorophenylboronic acid (45 mg, 0.26 mmol), tetrakis(triphenylphosphine)palladium (11 mg, 0.01 mmol) and potassium carbonate (81 mg, 0.6 mmol) were added into a 10 mL microwave vial containing a magnetic stirrer bar, followed by DME (1 mL) and $H_2O$ (0.2 mL). The vessel was sealed with a cap under an argon atmosphere, then the resulting mixture was heated to 90° C. for 40 mins under microwave. The mixture was cooled to room temperature and diluted with water (5 mL), extracted with ethyl acetate (10 mL×3), the combined organic layers were washed with brine (10 mL), dried over anhydrous sodium sulfate, concentrated in vacuo to give crude product, which was purified by C-18 reversed phase HPLC column to give desired 2-[5-(2-fluoro-5-methoxy-phenyl)-pyridin-3-ylamino]-2-phenyl-acetamide (15 mg) as a white solid.

Example 17

Preparation of 2-[5-(5-chloro-2-fluoro-phenyl)-pyridin-3-ylamino]-2-thiophen-3-yl-acetamide Step 1: Preparation of (5-bromo-pyridin-3-ylamino)-thiophen-3-yl-acetonitrile

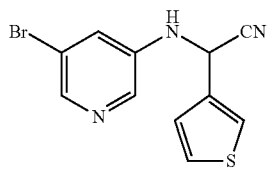 [SMILES: N#CC(Nc1cncc(Br)c1)c1ccsc1]

To a solution of 5-bromo-pyridin-3-ylamine (3.00 g, 17.3 mmol) and thiophene-3-carbaldehyde (2.34 g, 20.9 mmol) in DME (20 mL) was added TMSCN (2.58 g, 26.0 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-thiophen-3-yl-acetonitrile (3.63 g).

Step 2: Preparation of 2-(5-bromo-pyridin-3-ylamino)-2-thiophen-3-yl-acetamide

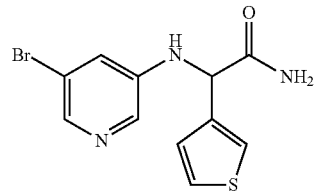 [SMILES: NC(=O)C(Nc1cncc(Br)c1)c1ccsc1]

A mixture of (5-bromo-pyridin-3-ylamino)-thiophen-3-yl-acetonitrile (2.4 g, 8.2 mmol) in conc. HCl (5 mL) was stirred at 40° C. for 30 mins. After the reaction was completed as monitored by TLC, water (200 mL) was added to the reaction mixture. The mixture was washed with EtOAc (100 mL×2). Then the aqueous solution was alkalized to pH=7.0-8.0 with concentrated ammonium hydroxide and extracted with EtOAc (100 mL×3). The organic layer was separated, washed with brine (100 mL), dried over $Na_2SO_4$, concentrated under reduced pressure to give 2-(5-bromo-pyridin-3-ylamino)-2-thiophen-3-yl-acetamide (1.3 g).

Step 3: Preparation of 2-[5-(5-chloro-2-fluoro-phenyl)-pyridin-3-ylamino]-2-thiophen-3-yl-acetamide To a solution of 2-(5-bromo-pyridin-3-ylamino)-2-thiophen-3-yl-acetamide (312 mg, 1.0 mmol) in DME-$H_2O$ (5:1, 6 mL) was added $Pd(PPh_3)_4$ (231 mg, 0.2 mmol), $K_2CO_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-thiophen-3-yl-acetamide (80 mg).

Example 18

Preparation of 2-[5-(5-chloro-2-fluoro-phenyl)-pyridin-3-ylamino]-2-p-tolyl-acetamide Step 1: Preparation of (5-bromo-pyridin-3-ylamino)-p-tolyl-acetonitrile

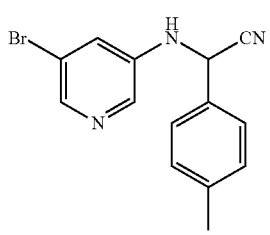 [SMILES: Cc1ccc(C(C#N)Nc2cncc(Br)c2)cc1]

To a solution of 5-bromo-pyridin-3-ylamine (7.00 g, 40.5 mmol) and 4-methyl-benzaldehyde (5.83 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-p-tolyl-acetonitrile (9.02 g).

Step 2: Preparation of 2-(5-bromo-pyridin-3-ylamino)-2-p-tolyl-acetamide

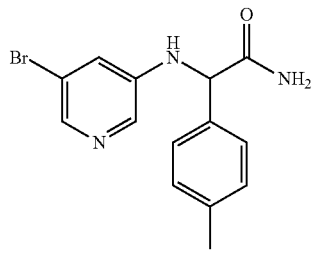 [SMILES: Cc1ccc(C(Nc2cncc(Br)c2)C(N)=O)cc1]

A mixture of (5-bromo-pyridin-3-ylamino)-p-tolyl-acetonitrile (3.00 g, 9.9 mmol) and conc. HCl (6 mL) was stirred at 40° C. for 1 h. Water (200 mL) was added to the reaction mixture. The mixture was washed with EtOAc (100 mL×2). Then the aqueous solution was alkalized to pH=7.0-8.0 with concentrated ammonium hydroxide and extracted with EtOAc (100 mL×3). The organic layer was separated, washed with brine (100 mL), dried over $Na_2SO_4$, concentrated under reduced pressure to give 2-(5-bromo-pyridin-3-ylamino)-2-p-tolyl-acetamide (2.16 g).

Step 3: Preparation of 2-[5-(5-chloro-2-fluoro-phenyl)-pyridin-3-ylamino]-2-p-tolyl-acetamide To a solution of 2-(5-bromo-pyridin-3-ylamino)-2-p-tolyl-acetamide (320 mg, 1.0 mmol) in DME-$H_2O$ (5:1, 6 mL) was added Pd(PPh$_3$)$_4$ (231 mg, 0.2 mmol), $K_2CO_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-p-tolyl-acetamide (36 mg).

Example 19

Preparation of 2-[5-(5-chloro-2-fluoro-phenyl)-pyridin-3-ylamino]-2-(3-chloro-phenyl)-acetamide

Step 1: Preparation of (5-bromo-pyridin-3-ylamino)-(3-chloro-phenyl)-acetonitrile

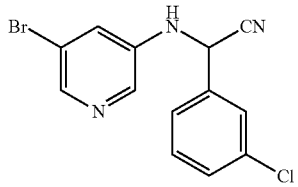 [SMILES: N#CC(Nc1cncc(Br)c1)c1cccc(Cl)c1]

To a solution of 5-bromo-pyridin-3-ylamine (7.00 g, 40.5 mmol) and 3-chloro-benzaldehyde (6.83 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-(3-chloro-phenyl)-acetonitrile (10.2 g).

Step 2: Preparation of 2-(5-bromo-pyridin-3-ylamino)-2-(3-chloro-phenyl)-acetamide

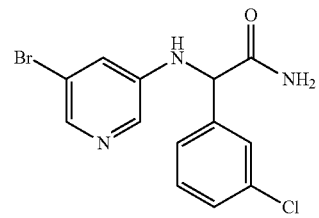 [SMILES: NC(=O)C(Nc1cncc(Br)c1)c1cccc(Cl)c1]

A mixture of (5-bromo-pyridin-3-ylamino)-(3-chlorophenyl)-acetonitrile (3.00 g, 9.3 mmol) and conc. HCl (6 mL) was stirred at 40° C. for 1 h. Water (200 mL) was added to the reaction mixture. The mixture was washed with EtOAc (100 mL×2). Then the aqueous solution was alkalized to pH=7.0-8.0 with concentrated ammonium hydroxide and extracted with EtOAc (100 mL×3). The organic layer was separated, washed with brine (100 mL), dried over $Na_2SO_4$, concentrated under reduced pressure to give 2-(5-bromo-pyridin-3-ylamino)-2-(3-chloro-phenyl)-acetamide (1.55 g).

Step 3: Preparation of 2-[5-(5-chloro-2-fluoro-phenyl)-pyridin-3-ylamino]-2-(3-chloro-phenyl)-acetamide To a solution of 2-(5-bromo-pyridin-3-ylamino)-2-(3-chloro-phenyl)-acetamide (340 mg, 1.0 mmol) in DME-$H_2O$ (5:1, 6 mL) was added Pd(PPh$_3$)$_4$ (231 mg, 0.2 mmol), $K_2CO_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-Chloro-2-fluoro-phenyl)-pyridin-3-ylamino]-2-(3-chloro-phenyl)-acetamide (18 mg).

Example 20

Preparation of 2-[5-(5-chloro-2-fluoro-phenyl)-pyridin-3-ylamino]-2-(4-chloro-phenyl)-acetamide

Step 1: Preparation of (5-bromo-pyridin-3-ylamino)-(4-chloro-phenyl)-acetonitrile

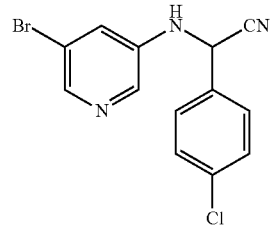 [SMILES: N#CC(Nc1cncc(Br)c1)c1ccc(Cl)cc1]

To a solution of 5-bromo-pyridin-3-ylamine (7.00 g, 40.5 mmol) and 4-chloro-benzaldehyde (6.83 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-(4-chloro-phenyl)-acetonitrile (8.10 g).

Step 2: Preparation of 2-(5-bromo-pyridin-3-ylamino)-2-(4-chloro-phenyl)-acetamide

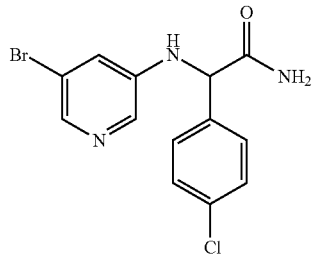 [SMILES: NC(=O)C(Nc1cncc(Br)c1)c1ccc(Cl)cc1]

A mixture of (5-bromo-pyridin-3-ylamino)-(4-chloro-phenyl)-acetonitrile (3.00 g, 9.3 mmol) and conc. HCl (6 mL) was stirred at 40° C. for 1.5 hrs. Water (200 mL) was added to the reaction mixture. The mixture was washed with EtOAc (100 mL×2). Then the aqueous solution was alkalized to pH=7.0-8.0 with concentrated ammonium hydroxide and then extracted with EtOAc (100 mL×3). The organic layer was separated, washed with brine (100 mL), dried over $Na_2SO_4$, concentrated under reduced pressure to give 2-(5-bromo-pyridin-3-ylamino)-2-(4-chloro-phenyl)-acetamide (1.21 g).

Step 3: Preparation of 2-[5-(5-chloro-2-fluoro-phenyl)-pyridin-3-ylamino]-2-(4-chloro-phenyl)-acetamide To a solution of 2-(5-bromo-pyridin-3-ylamino)-2-(4-chloro-phenyl)-acetamide (340 mg, 1.0 mmol) in DME-$H_2O$ (5:1, 6 mL) was added Pd(PPh$_3$)$_4$ (231 mg, 0.2 mmol), $K_2CO_3$ (276 mg, 2.0 mmol) and 5-chloro-2-fluorophenyl-boronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-(-chloro-phenyl)-acetamide (35 mg).

Example 21

Preparation of 2-[5-(5-chloro-2-fluoro-phenyl)-pyridin-3-ylamino]-2-(3-methoxy-phenyl)-acetamide Step 1: Preparation of (5-bromo-pyridin-3-ylamino)-(3-methoxy-phenyl)-acetonitrile

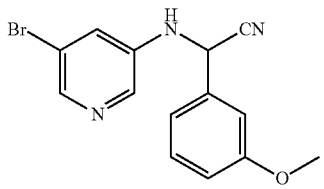 [SMILES: COc1cccc(C(C#N)Nc2cncc(Br)c2)c1]

To a solution of 5-bromo-pyridin-3-ylamine (7.00 g, 40.5 mmol) and 3-methoxy-benzaldehyde (6.62 g, 48.6 mmol) in DME (50 mL) was added TMSCN (6.03 g, 60.8 mmol) dropwise at room temperature. The reaction mixture was refluxed for 16 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-(3-methoxy-phenyl)-acetonitrile (9.41 g).

Step 2: Preparation of 2-(5-bromo-pyridin-3-ylamino)-2-(3-methoxy-phenyl)-acetamide

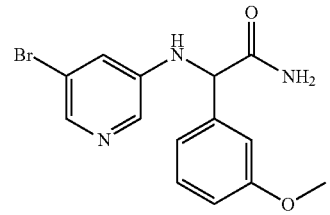 [SMILES: COc1cccc(C(Nc2cncc(Br)c2)C(N)=O)c1]

A mixture of (5-bromo-pyridin-3-ylamino)-(3-methoxy-phenyl)-acetonitrile (3.00 g, 9.4 mmol) and conc. HCl (6 mL) was stirred at 40° C. for 1.5 hrs. Water (200 mL) was added to the reaction mixture. The mixture was washed with EtOAc (100 mL×2). Then the aqueous solution was alkalized to pH=7.0-8.0 with concentrated ammonium hydroxide and then extracted with EtOAc (100 mL×3). The organic layer was separated, washed with brine (100 mL), dried over $Na_2SO_4$, concentrated under reduced pressure to give 2-(5-bromo-pyridin-3-ylamino)-2-(3-methoxy-phenyl)-acetamide (1.61 g).

Step 3: Preparation of 2-[5-(5-chloro-2-fluoro-phenyl)-pyridin-3-ylamino]-2-(3-methoxy-phenyl)-acetamide To a solution of 2-(5-bromo-pyridin-3-ylamino)-2-(3-methoxy-phenyl)-acetamide (340 mg, 1.0 mmol) in DME-$H_2O$ (5:1, 6 mL) was added Pd(PPh$_3$)$_4$ (231 mg, 0.2 mmol), $K_2CO_3$ (276 mg, 2.0 mmol) and 5-chloro-2-fluorophenyl-boronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-(3-methoxy-phenyl)-acetamide (75 mg).

Example 22

Preparation of N-{2-[5-(5-chloro-2-fluoro-phenyl)-pyridin-3-ylamino]-2-phenyl-acetyl}-methanesulfonamide Step 1: Preparation of (R)-[5-(5-chloro-2-fluoro-phenyl)-pyridin-3-ylamino]-phenyl-acetic acid

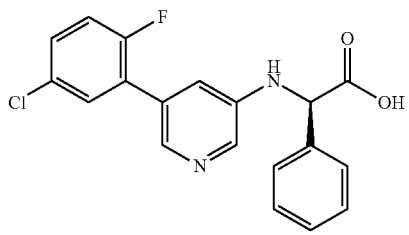 [SMILES: O=C(O)[C@H](Nc1cncc(-c2cc(Cl)ccc2F)c1)c1ccccc1]

(R)-(5-Bromo-pyridin-3-ylamino)-phenyl-acetic acid (306 mg, 1 mmol), 3-chloro-2-fluorophenylboronic acid (365 mg, 2.1 mmol), tetrakis(triphenylphosphine) palladium (58 mg, 0.05 mmol) and potassium phosphate (848 mg, 4 mmol) were added into a 35 mL microwave vial containing a magnetic stirrer bar, followed by DME (5 mL) and H₂O (1 mL). The vessel was sealed with a cap under an argon atmosphere, and then the resulting mixture was heated to 90° C. for 55 mins under microwave. The reaction mixture was cooled to room temperature. DME was removed in vacuo, then the residue was basified by 2 NNaOH aq. to PH=12. Then the mixture was extracted with ethyl acetate (20 mL), the separated aqueous layers was acidified by conc. HCl to PH=2, then extracted with ethyl acetate (30 mL×3), the combined organic layers were washed with brine (10 mL), dried over anhydrous sodium sulfate, concentrated in vacuo to afford crude (R)-[5-(5-chloro-2-fluoro-phenyl)-pyridin-3-ylamino]-phenyl-acetic acid (397 mg) as a yellow oil which was directly used for next step without further purification.

Step 2: Preparation of N-{2-[5-(5-chloro-2-fluoro-phenyl)-pyridin-3-ylamino]-2-phenyl-acetyl}-methanesulfonamide To a solution of crude (R)-[5-(5-chloro-2-fluoro-phenyl)-pyridin-3-ylamino]-phenyl-acetic acid (397 mg, 1 mmol) in DMF (3 mL) was added HATU (760 mg, 2 mmol), followed by N,N-diisopropylethylamine (516 mg, 4 mmol), the resulting mixture was stirred at room temperature for 10 minutes. Then methanesulfonamide (380 mg, 4 mmol) in DMF (2 mL) was added and the mixture was stirred at room temperature overnight. The reaction mixture was directly purified by C-18 reversed phase HPLC column to give desired N-{2-[5-(5-chloro-2-fluoro-phenyl)-pyridin-3-ylamino]-2-phenyl-acetyl}-methanesulfonamide (30 mg) as a white solid.

Example 23

Preparation of 2-[5-(5-chloro-2,4-difluoro-phenyl)-pyridin-3-ylamino]-2-phenyl-acetamide 2-(5-Bromo-pyridin-3-ylamino)-2-phenyl-acetamide (60 mg, 0.2 mmol), 5-chloro-2,4-difluorophenylboronic acid (50 mg, 0.26 mmol), tetrakis(triphenylphosphine)palladium (11 mg, 0.01 mmol) and potassium carbonate (81 mg, 0.6 mmol) were added into a 10 mL microwave vial containing a magnetic stirrer bar, followed by DME (1 mL) and H₂O (0.2 mL). The vessel was sealed with a cap under an argon atmosphere, and then the resulting mixture was heated to 90° C. for 40 mins under microwave. The mixture was cooled to room temperature and diluted with water (5 mL), then extracted with ethyl acetate (10 mL×3), the combined organic layers were washed with brine (10 mL), dried over anhydrous sodium sulfate, concentrated in vacuo to give crude product which was purified by C-18 reversed phase HPLC column to give desired 2-[5-(5-chloro-2,4-difluoro-phenyl)-pyridin-3-ylamino]-2-phenyl-acetamide (49 mg) as a white solid.

Example 24

Preparation of 2-[5-(5-chloro-2-fluoro-phenyl)-pyridin-3-ylamino]-2-pyridin-2-yl-acetamide Step 1: Preparation of (5-bromo-pyridin-3-ylamino)-pyridin-2-yl-acetonitrile

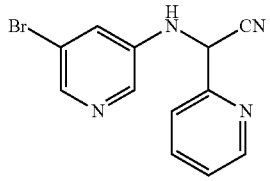 [SMILES: N#CC(Nc1cncc(Br)c1)c1ccccn1]

To a solution of 5-bromo-pyridin-3-ylamine (7.00 g, 40.5 mmol) and pyridine-2-carbaldehyde (5.20 g, 48.6 mmol) in DME (50 mL) was added TMSCN (6.03 g, 60.8 mmol) dropwise at room temperature. The reaction mixture was refluxed for 24 hrs. After the reaction was completed as monitored by TLC, the reaction solution was concentrated. The residue was purified through Chemflash, eluted with a gradient from 0% to 40% EtOAc in petroleum ether to give (5-bromo-pyridin-3-ylamino)-pyridin-2-yl-acetonitrile (5.25 g).

Step 2: Preparation of 2-(5-bromo-pyridin-3-ylamino)-2-pyridin-2-yl-acetamide

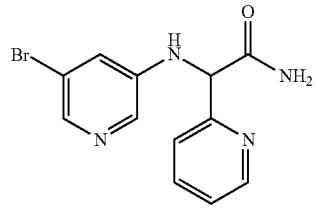 [SMILES: NC(=O)C(Nc1cncc(Br)c1)c1ccccn1]

A mixture of (5-bromo-pyridin-3-ylamino)-pyridin-2-yl-acetonitrile (3.00 g, 10.4 mmol) and conc. HCl (6 mL) was stirred at 40° C. for 1 h. Water (200 mL) was added to the reaction mixture. The mixture was washed with EtOAc (100 mL×2). Then the aqueous solution was alkalized to pH=7.0-8.0 with concentrated ammonium hydroxide and extracted with EtOAc (100 mL×3). The organic layer was separated, washed with brine (100 mL), dried over Na₂SO₄, concentrated under reduced pressure to give 2-(5-bromo-pyridin-3-ylamino)-2-pyridin-2-yl-acetamide (1.18 g).

Step 3: Preparation of 2-[5-(5-chloro-2-fluoro-phenyl)-pyridin-3-ylamino]-2-pyridin-2-yl-acetamide To a solution of 2-(5-bromo-pyridin-3-ylamino)-2-pyridin-2-yl-acetamide (306 mg, 1.0 mmol) in DME-H2O (5:1, 6 mL) was added Pd(PPh₃)₄ (231 mg, 0.2 mmol), K₂CO₃ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-pyridin-2-yl-acetamide (45 mg).

Example 25

Preparation of 2-[5-(5-chloro-2-fluoro-phenyl)-pyridin-3-ylamino]-2-thiophen-2-yl-acetamide Step 1: Preparation of (5-bromo-pyridin-3-ylamino)-thiophen-3-yl-acetonitrile

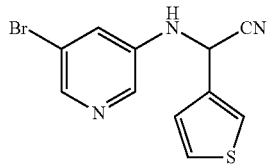

To a solution of 5-bromo-pyridin-3-ylamine (3.00 g, 17.3 mmol) and thiophene-3-carbaldehyde (2.34 g, 20.9 mmol) in DME (20 mL) was added TMSCN (2.58 g, 26.0 mmol) dropwise at room temperature. The reaction mixture was refluxed for 16 hrs. Upon the completion of the reaction which was monitored by TLC, the reaction solution was concentrated. The residue was purified through Chemflash, eluted with a gradient from 0% to 40% EtOAc in petroleum ether to give (5-bromo-pyridin-3-ylamino)-thiophen-3-yl-acetonitrile (3.63 g).

Step 2: Preparation of 2-(5-bromo-pyridin-3-ylamino)-2-thiophen-2-yl-acetamide

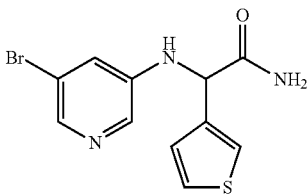

A mixture of (5-bromo-pyridin-3-ylamino)-thiophen-3-yl-acetonitrile (2.4 g, 8.2 mmol) in conc. HCl (5 mL) was stirred at 40° C. for 30 min. After the reaction was completed as monitored by TLC, water (200 mL) was added to the reaction mixture. The mixture was washed with EtOAc (100 mL×2). Then the aqueous solution was alkalized to pH=7.0-8.0 with concentrated ammonium hydroxide and then extracted with EtOAc (100 mL×3). The organic layer was separated, washed with brine (100 mL), dried over $Na_2SO_4$, concentrated under reduced pressure to give 2-(5-bromo-pyridin-3-ylamino)-2-thiophen-2-yl-acetamide (1.3 g).

Step 3: Preparation of 2-[5-(5-chloro-2-fluoro-phenyl)-pyridin-3-ylamino]-2-thiophen-2-yl-acetamide To a solution of 2-(5-cromo-pyridin-3-ylamino)-2-thiophen-2-yl-acetamide (327 mg, 1.0 mmol) in DME-$H_2O$ (5:1, 6 mL) was added Pd(PPh$_3$)$_4$ (231 mg, 0.2 mmol), $K_2CO_3$ (276 mg, 2.0 mmol) and 5-chloro-2-fluorophenylboronic acid (210 mg, 1.2 mmol). The resulting mixture was degassed and then stirred for 10 hrs at 80° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[5-(5-chloro-2-fluoro-phenyl)-pyridin-3-ylamino]-2-thiophen-2-yl-acetamide (45 mg).

Example 26

Preparation of 2-[6-(3-chloro-4-hydroxy-phenyl)-pyrazin-2-ylamino]-2-phenyl-acetamide Step 1: Preparation of 2-(6-pyrazin-2-ylamino)-2-phenyl-acetamide

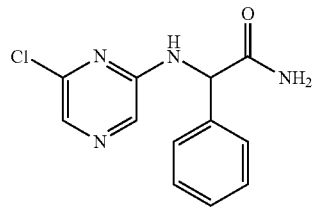 [SMILES: NC(=O)C(Nc1cncc(Cl)n1)c1ccccc1]

To a solution of 2,6-dichloropyrazine (14.9 g, 0.1 mol) in acetonitrile (100 mL) was added D(–) phenylglycinamide (18 g, 0.12 mol) and triethylamine (20.2 g, 0.2 mol). The resulting mixture was stirred at 75° C. for 48 hrs. After the reaction was completed as monitored by LC-MS, the reaction mixture was cooled and then the solvent was removed, and the residue was partitioned between EtOAc and water. The aqueous layer was separated and extracted with EtOAc. The combined organic layers were washed by water and brine, dried, concentrated. The residue was purified by column chromatography (EtOAc/PE=2:1) to give 2-(6-pyrazin-2-ylamino)-2-phenyl-acetamide (6.5 g).

Step 2: Preparation of 2-[6-(3-chloro-4-hydroxy-phenyl)-pyrazin-2-ylamino]-2-phenyl-acetamide Under an Ar atmosphere, a mixture of 2-(6-chloro-pyrazin-2-ylamino)-2-phenyl-acetamide (170 mg, 0.65 mmol), 3-chloro-4-hydroxyphenylboronic acid pinacol ester (200 mg, 0.78 mmol), Pd(PPh$_3$)$_2$Cl$_2$ (45 mg, 0.065 mmol), 2-(dicyclohexyphosphino)biphenyl (45 mg, 0.13 mmol) and $Na_2CO_3$ (140 mg, 1.3 mmol) in DME-$H_2O$ (5:1, 3 mL) was exposed to microwave irradiation at 130° C. for 30 mins, then concentrated in vacuo. The residue was partitioned between EtOAc and brine. The aqueous layer was separated and extracted with EtOAc. The combined organic layers were concentrated and the residue was purified by Prep-HPLC to give 2-[6-(3-chloro-4-hydroxy-phenyl)-pyrazin-2-ylamino]-2-phenyl-acetamide (12 mg).

Example 27

Preparation of (R)-2-[6-(3-chloro-4-hydroxy-phenyl)-pyrazin-2-ylamino]-2-phenyl-acetamide Separation of the two enantiomers from 2-[6-(3-chloro-4-hydroxy-phenyl)-pyrazin-2-ylamino]-2-phenyl-acetamide (25 mg) was conducted by chiral SFC to provide chiral (R)-2-[6-(3-chloro-4-hydroxy-phenyl)-pyrazin-2-ylamino]-2-phenyl-acetamide (4 mg).

Example 28

Preparation of (S)-2-[6-(3-chloro-4-hydroxy-phenyl)-pyrazin-2-ylamino]-2-phenyl-acetamide Separation of the two enantiomers from 2-[6-(3-chloro-4-hydroxy-phenyl)-pyrazin-2-ylamino]-2-phenyl-acetamide

45

(25 mg) was conducted by chiral SFC to provide chiral (S)-2-[6-(3-chloro-4-hydroxy-phenyl)-pyrazin-2-ylamino]-2-phenyl-acetamide (6 mg).

Example 29

Preparation of 2-[6-(5-chloro-2-fluoro-phenyl)-pyrazin-2-ylamino]-2-phenyl-acetamide To a solution of 2-(6-chloro-pyrazin-2-ylamino)-2-phenyl-acetamide (170 mg, 0.65 mmol) in DME-H2O (5:1, 6 mL) was added Pd(PPh$_3$)$_4$ (150 mg, 0.13 mmol), K$_2$CO$_3$ (180 mg, 1.3 mmol) and 5-chloro-2-fluorophenyl boronic acid (170 mg, 0.975 mmol). The resulting mixture was degassed and then stirred for 10 hrs at 85° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[6-(5-chloro-2-fluoro-phenyl)-pyrazin-2-ylamino]-2-phenyl-acetamide (50 mg).

Example 30

Preparation of (R)-2-[6-(5-chloro-2-fluoro-phenyl)-pyrazin-2-ylamino]-2-phenyl-acetamide Separation of the two enantiomers from -2-[6-(5-chloro-2-fluoro-phenyl)-pyrazin-2-ylamino]-2-phenyl-acetamide (10 mg) was conducted by chiral SFC to provide chiral (R)-2-[6-(5-chloro-2-fluoro-phenyl)-pyrazin-2-ylamino]-2-phenyl-acetamide (2 mg).

Example 31

Preparation of (S)-2-[6-(5-chloro-2-fluoro-phenyl)-pyrazin-2-ylamino]-2-phenyl-acetamide Separation of the two enantiomers from 2-[6-(5-chloro-2-fluoro-phenyl)-pyrazin-2-ylamino]-2-phenyl-acetamide (10 mg) was conducted by chiral SFC to provide chiral (S)-2-[6-(5-chloro-2-fluoro-phenyl)-pyrazin-2-ylamino]-2-phenyl-acetamide (1 mg).

Example 32

Preparation of 2-[6-(3-methoxy-phenyl)-pyrazin-2-ylamino]-2-phenyl-acetamide

To a solution of 2-(6-chloro-pyrazin-2-ylamino)-2-phenyl-acetamide (170 mg, 0.65 mmol) in DME-H$_2$O (5:1, 6 mL) was added Pd(PPh$_3$)$_4$ (150 mg, 0.13 mmol), K$_2$CO$_3$ (180 mg, 1.3 mmol) and 3-methoxyphenylboronic acid (150 mg, 0.975 mmol). The resulting mixture was degassed and then stirred for 10 hrs at 85° C. under an Ar atmosphere. After the reaction was completed as monitored by LC-MS, the mixture was diluted with water and then extracted with EtOAc. The combined organic layers were washed with water and brine, and then dried. The solvent was concentrated and the residue was purified by Prep-HPLC to give 2-[6-(3-methoxy-phenyl)-pyrazin-2-ylamino]-2-phenyl-acetamide (45 mg).

46

Example 33

Preparation of (R)-2-[6-(3-methoxy-phenyl)-pyrazin-2-ylamino]-2-phenyl-acetamide Separation of the two enantiomers from 2-[6-(3-methoxy-phenyl)-pyrazin-2-ylamino]-2-phenyl-acetamide (45 mg) was conducted by chiral SFC to provide chiral (R)-2-[6-(3-methoxy-phenyl)-pyrazin-2-ylamino]-2-phenyl-acetamide (18 mg).

BIOLOGICAL EXAMPLES

Example 34

CDK8/Cyclin C LANCE TR-FRET Kinase Assay

The biological activity of the compounds of the invention can be determined using the assay described below.

CDK8/Cyclin C protein was obtained from Invitrogen, cat #PV4402. ULight-Glycogen Synthase (Ulight-GS) peptide with sequence PASVPPSPSLSRHSSPHQ(pS)ED, and Europium-anti-phospho Glycogen Synthase (Ser641) [Eu-anti-P-GS (Ser641)] were obtained from Perkin Elmer, cat #TRF0131-M and cat #TRF0220. Adenosine-5'-triphosphate (ATP) was obtained from Invitrogen, cat #PV3227.

A mixture of (1) a compound of formula I, (2) substrate [Ulight-GS peptide (80 nM) and ATP (24 μM)], and (3) CDK8/Cyclin C (10 nM) in reaction buffer (50 mM Hepes, pH7.0, 10 mM MgCl$_2$, 1 mM EGTA, 0.2 mg/mL BSA, 0.8 mM DTT) were incubated at 37° C. for 30 mins. Then, [Eu-anti-P-GS (Ser641)] (1.5 nM) was added. Following incubation at RT for 30 mins, the TR-FRET signals were detected using Envision reader (Ex 340 nm, Em 615 nm and 665 nm) from Perkin Elmer. The reactivity in percentage of inhibition or dose response was analyzed with GraphPad Prism 5 (GraphPad Software).

Results of CDK8/Cyclin LANCE Ultra biochemical TR-FRET kinase assay are given in Table 1.

Example 35

In Vitro Cell Proliferation Assay

Cells were seeded on 96-well plates at 5×10$^3$ cells per well and precultured for 24 hours. The cells were treated with serial diluted compounds and cultured for 72 hours. Then all media was discarded and after that, 100 μL 1:10 (v/v) Cell Counting Kit-8 (CCK-8)-culture media solution was added to the wells. Plate was developed for 2 hrs in an incubator, and the absorbance was measured at 450 nm wavelengths with SpectraMAX190 (MDS, Sunnyvale, Calif.). The inhibition rate (IR) of the tested compounds was determined with following formula: IR (%)=(OD$_{DMSO}$−ODcompound)/OD$_{DMSO}$×100%. The concentration corresponding to 50% IR (IC$_{50}$) was determined with plot curve of IR against tested compound concentrations with SoftMax Pro.

Results of in vitro cell proliferation assay are given in Table 3.

Example A

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. Compounds of formula (I)

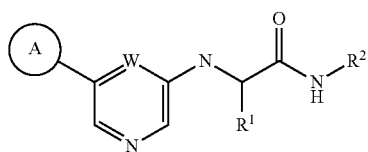

(I)

wherein $R^1$ is phenyl, pyridinyl, thienyl, pyrimidinyl, pyrazolyl, pyridinonyl or pyrrolyl; which is unsubstituted or once or twice substituted by $C_{1-6}$alkoxy, $C_{1-6}$alkyl, halogen or trifluoromethyl;

$R^2$ is hydrogen, $C_{1-6}$alkyl, $C_{1-6}$alkylcarbonyl or $C_{1-6}$alkylsulfonyl;

A is phenyl, pyridinyl, pyridinonyl, thienyl, pyrazolyl or pyrrolyl; which is unsubstituted or once or twice or thrice substituted by $C_{1-6}$alkoxy, $C_{1-6}$alkyl, cyano, halogen, hydroxy or trifluoromethyl;

W is —N— or —CH;

or pharmaceutically acceptable salt thereof.

2. A compound according to claim 1, wherein $R^1$ is phenyl, which is unsubstituted or once or twice substituted by $C_{1-6}$alkoxy, $C_{1-6}$alkyl or halogen; pyridinyl; or thienyl;

$R^2$ is hydrogen or $C_{1-6}$alkylsulfonyl;

A is phenyl or pyridinyl; which is once or twice or thrice substituted by $C_{1-6}$alkoxy, $C_{1-6}$alkyl, halogen or hydroxy;

W is —N— or —CH;

or pharmaceutically acceptable salt thereof.

3. A compound according to claim 2, wherein $R^1$ is phenyl, which is unsubstituted or once or twice substituted by methoxy, methyl, fluoro or chloro; pyridinyl; or thienyl;

$R^2$ is hydrogen or methylsulfonyl;

A is phenyl or pyridinyl; which is once or twice or thrice substituted by ethoxy, methoxy, methyl, fluoro, chloro or hydroxy;

W is —N— or —CH;

or pharmaceutically acceptable salt thereof.

4. A compound according to claim 2, wherein $R^1$ is phenyl, which is unsubstituted or once or twice substituted by $C_{1-6}$alkoxy, $C_{1-6}$alkyl or halogen; pyridinyl; or thienyl;

$R^2$ is hydrogen;

A is phenyl or pyridinyl; which is once or twice or thrice substituted by $C_{1-6}$alkoxy, $C_{1-6}$alkyl, halogen or hydroxy;

W is —CH; or pharmaceutically acceptable salt thereof.

5. A compound according to claim 4, wherein $R^1$ is phenyl, which is unsubstituted or once or twice substituted by methoxy, methyl, fluoro or chloro; pyridinyl; or thienyl;

$R^2$ is hydrogen;

A is phenyl or pyridinyl; which is once or twice or thrice substituted by ethoxy, methoxy, methyl, fluoro, chloro or hydroxy;

W is —CH; or pharmaceutically acceptable salt thereof.

6. A compound according to claim 2, wherein $R^1$ is phenyl;

$R^2$ is hydrogen;

A is phenyl, which is once or twice substituted by $C_{1-6}$alkoxy, halogen or hydroxy;

W is —N; or pharmaceutically acceptable salt thereof.

7. A compound according to claim 6, wherein $R^1$ is phenyl;

$R^2$ is hydrogen;

A is phenyl, which is once or twice substituted by methoxy, fluoro, chloro or hydroxy;

W is —N; or pharmaceutically acceptable salt thereof.

8. A compound according to claim 1, selected from (R)-2-[5-(5-Chloro-2-fluoro-phenyl)-pyridin-3-ylamino]-2-phenyl-cetamide;

2-[5-(3-Chloro-4-hydroxy-phenyl)-pyridin-3-ylamino]-2-phenyl-acetamide;

(R)-2-[5-(3-Chloro-4-hydroxy-phenyl)-pyridin-3-ylamino]-2-phenyl-acetamide;

(S)-2-[5-(3-Chloro-4-hydroxy-phenyl)-pyridin-3-ylamino]-2-phenyl-acetamide;

2-(4'-Methyl-[3,3']bipyridinyl-5-ylamino)-2-phenyl-acetamide;

2-(2'-Methoxy-[3,4']bipyridinyl-5-ylamino)-2-phenyl-acetamide;

2-[5-(5-Ethoxy-2-fluoro-phenyl)-pyridin-3-ylamino]-2-phenyl-acetamide;

2-[5-(3-Chloro-4-fluoro-phenyl)-pyridin-3-ylamino]-2-phenyl-acetamide;

2-(5'-Fluoro-2'-methoxy-[3,4']bipyridinyl-5-ylamino)-2-phenyl-acetamide;

2-(5'-Chloro-[3,3']bipyridinyl-5-ylamino)-2-phenyl-acetamide;

2-[5-(5-Chloro-2-fluoro-phenyl)-pyridin-3-ylamino]-2-o-tolyl-acetamide;

2-[5-(5-Chloro-2-fluoro-phenyl)-pyridin-3-ylamino]-2-(2-fluoro-phenyl)-acetamide;

2-[5-(5-Chloro-2-fluoro-phenyl)-pyridin-3-ylamino]-2-m-tolyl-acetamide;
2-[5-(5-Chloro-2-fluoro-phenyl)-pyridin-3-ylamino]-2-(2-chloro-phenyl)-acetamide;
2-[5-(5-Chloro-2-fluoro-phenyl)-pyridin-3-ylamino]-2-(2,5-difluoro-phenyl)-acetamide;
2-[5-(2-Fluoro-5-methoxy-phenyl)-pyridin-3-ylamino]-2-phenyl-acetamide;
2-[5-(5-Chloro-2-fluoro-phenyl)-pyridin-3-ylamino]-2-thiophen-3-yl-acetamide;
2-[5-(5-Chloro-2-fluoro-phenyl)-pyridin-3-ylamino]-2-p-tolyl-acetamide;
2-[5-(5-Chloro-2-fluoro-phenyl)-pyridin-3-ylamino]-2-(3-chloro-phenyl)-acetamide;
2-[5-(5-Chloro-2-fluoro-phenyl)-pyridin-3-ylamino]-2-(4-chloro-phenyl)-acetamide;
2-[5-(5-Chloro-2-fluoro-phenyl)-pyridin-3-ylamino]-2-(3-methoxy-phenyl)-acetamide;
N-{2-[5-(5-Chloro-2-fluoro-phenyl)-pyridin-3-ylamino]-2-phenyl-acetyl}-methanesulfonamide;
2-[5-(5-Chloro-2,4-difluoro-phenyl)-pyridin-3-ylamino]-2-phenyl-acetamide;
2-[5-(5-Chloro-2-fluoro-phenyl)-pyridin-3-ylamino]-2-pyridin-2-yl-acetamide;
2-[5-(5-Chloro-2-fluoro-phenyl)-pyridin-3-ylamino]-2-thiophen-2-yl-acetamide;
2-[6-(3-Chloro-4-hydroxy-phenyl)-pyrazin-2-ylamino]-2-phenyl-acetamide;
(R)-2-[6-(3-Chloro-4-hydroxy-phenyl)-pyrazin-2-ylamino]-2-phenyl-acetamide;
(S)-2-[6-(3-Chloro-4-hydroxy-phenyl)-pyrazin-2-ylamino]-2-phenyl-acetamide;
2-[6-(5-Chloro-2-fluoro-phenyl)-pyrazin-2-ylamino]-2-phenyl-acetamide;
(R)-2-[6-(5-Chloro-2-fluoro-phenyl)-pyrazin-2-ylamino]-2-phenyl-acetamide;
(S)-2-[6-(5-Chloro-2-fluoro-phenyl)-pyrazin-2-ylamino]-2-phenyl-acetamide;
2-[6-(3-Methoxy-phenyl)-pyrazin-2-ylamino]-2-phenyl-acetamide; and
(R)-2-[6-(3-Methoxy-phenyl)-pyrazin-2-ylamino]-2-phenyl-acetamide; or pharmaceutically acceptable salt thereof.

9. A process for the preparation of a compound according to claim 1 comprising the reaction of
(a) a compound of formula (A)

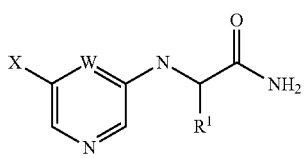
(A)

with

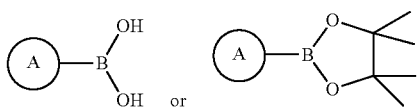

in the presence of a catalyst and a base;
(b) a compound of formula (B)

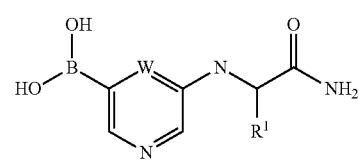
(B)

with

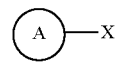

in the presence of a catalyst and a base;
(c) a compound of formula (C)

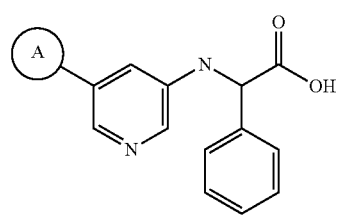
(C)

with $C_{1-6}$alkylsulfonyl amides in the presence of HATU/DIPEA;
wherein $R^1$, $R^2$, W and A are defined as in any one of claims 1 to 7; X is chloro, bromo or iodo.

10. A pharmaceutical composition comprising a compound of claim 1 or pharmaceutically acceptable salt thereof and a therapeutically inert carrier.

11. A method for the treatment of cancer, which method comprises administering an effective amount of a compound of claim 1 or pharmaceutically acceptable salt thereof to a patient in need thereof.

12. The method of claim 11, wherein said cancer is bladder, head and neck, breast, stomach, ovary, colon, lung, brain, larynx, lymphatic system, liver, skin, hematopoetic system, genitourinary tract, gastrointestinal, ovarian, prostate, gastric, bone, small-cell lung, glioma, colorectal and pancreatic cancers.

13. The method of claim 12, wherein said cancer is gastric cancer or colorectal cancer.

* * * * *